US012588921B2

(12) United States Patent
Kitamura et al.

(10) Patent No.: US 12,588,921 B2
(45) Date of Patent: Mar. 31, 2026

(54) TREATMENT TOOL, TREATMENT TOOL ASSEMBLING METHOD, AND TREATMENT TOOL DISASSEMBLING METHOD

(71) Applicant: OLYMPUS CORPORATION, Hachioji (JP)

(72) Inventors: Ojiro Kitamura, Hachioji (JP); Yuki Kawaguchi, Koshu (JP)

(73) Assignee: Olympus Corporation, Tokyo (JP)

( * ) Notice: Subject to any disclaimer, the term of this patent is extended or adjusted under 35 U.S.C. 154(b) by 807 days.

(21) Appl. No.: 17/854,705

(22) Filed: Jun. 30, 2022

(65) Prior Publication Data

US 2022/0330966 A1        Oct. 20, 2022

Related U.S. Application Data

(63) Continuation of application No. PCT/JP2020/018469, filed on May 1, 2020.

(51) Int. Cl.
A61B 17/29        (2006.01)

(52) U.S. Cl.
CPC ...... A61B 17/29 (2013.01); *A61B 2017/2903* (2013.01); *A61B 2017/2931* (2013.01); *A61B 2017/2947* (2013.01)

(58) Field of Classification Search
CPC .... A61B 2017/2931; A61B 2017/2947; A61B 2017/294; A61B 2017/2926; A61B 2017/2936; A61B 17/29
See application file for complete search history.

(56) References Cited

U.S. PATENT DOCUMENTS

| | | | |
|---|---|---|---|
| 5,290,309 A | 3/1994 | Kothe | |
| 6,019,780 A * | 2/2000 | Lombardo | ......... A61B 17/1608 606/174 |
| 6,214,023 B1 * | 4/2001 | Whipple | ........ A61B 17/320092 606/169 |
| 2013/0046337 A1 | 2/2013 | Evans et al. | |

FOREIGN PATENT DOCUMENTS

| | | |
|---|---|---|
| JP | H05-115488 A | 5/1993 |
| JP | 2004-313540 A | 11/2004 |
| WO | 2019/224952 A1 | 11/2019 |

OTHER PUBLICATIONS

Jul. 14, 2020 International Search Report issued in International Patent Application No. PCT/JP2020/018469.

* cited by examiner

*Primary Examiner* — Katherine H Schwiker
(74) *Attorney, Agent, or Firm* — OLIFF PLC

(57)        ABSTRACT

A treatment tool includes: a sheath extending along a longitudinal axis; a fixed gripping piece protruding from a distal end of the sheath; a movable gripping piece that is movably attached to either the sheath or the fixed gripping piece, the movable gripping piece being configured to grip a living tissue between the movable gripping piece and the fixed gripping piece; and a movement restricting portion configured to allow movement of the movable gripping piece in a first range and restrict movement of the movable gripping piece in a second range different from the first range. The movable gripping piece is attachable to and detachable from either the sheath or the fixed gripping piece at a movement position within the second range.

19 Claims, 24 Drawing Sheets

FIG.29

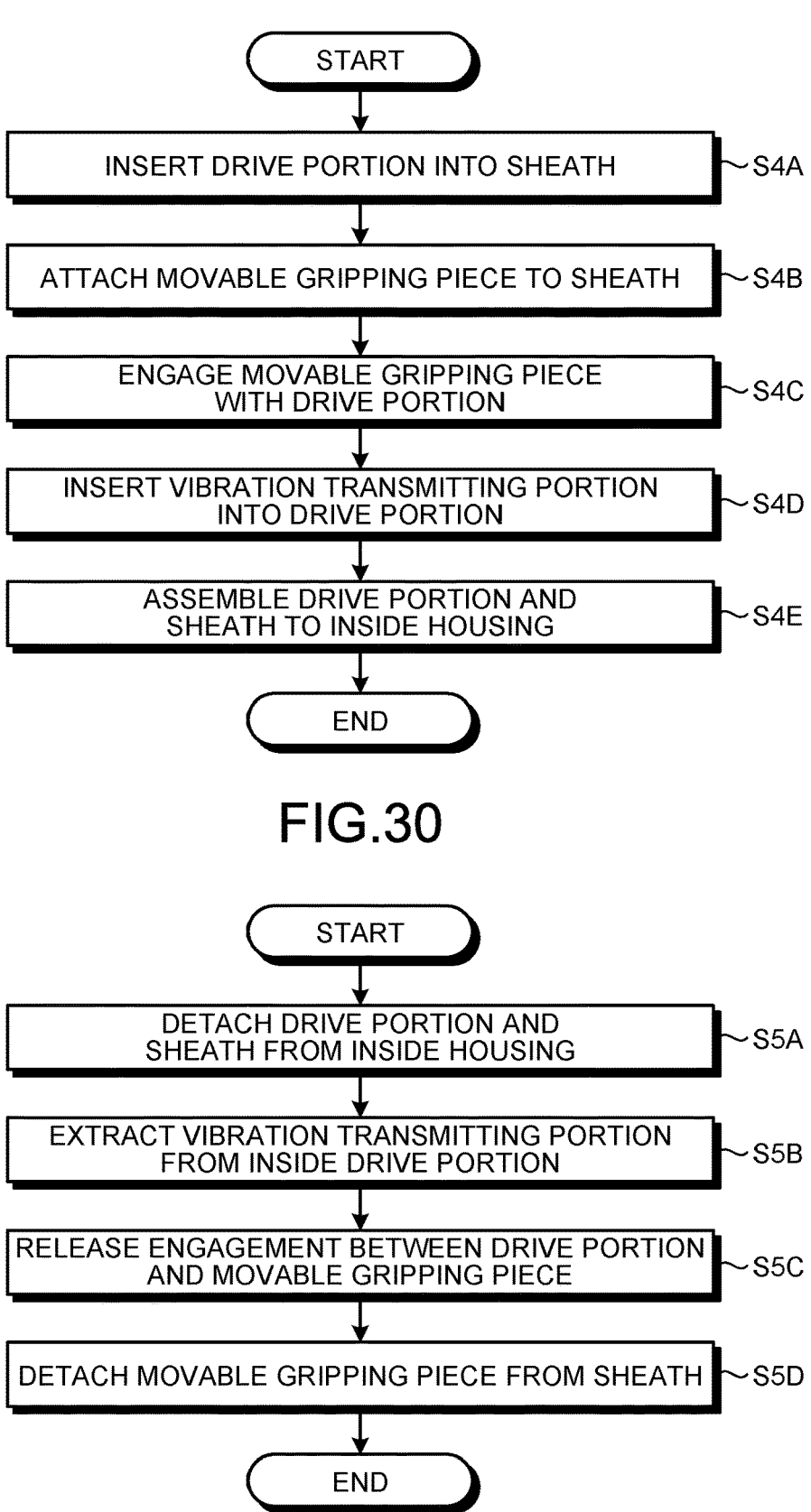

START

INSERT DRIVE PORTION INTO SHEATH — S4A

ATTACH MOVABLE GRIPPING PIECE TO SHEATH — S4B

ENGAGE MOVABLE GRIPPING PIECE WITH DRIVE PORTION — S4C

INSERT VIBRATION TRANSMITTING PORTION INTO DRIVE PORTION — S4D

ASSEMBLE DRIVE PORTION AND SHEATH TO INSIDE HOUSING — S4E

END

FIG.30

START

DETACH DRIVE PORTION AND SHEATH FROM INSIDE HOUSING — S5A

EXTRACT VIBRATION TRANSMITTING PORTION FROM INSIDE DRIVE PORTION — S5B

RELEASE ENGAGEMENT BETWEEN DRIVE PORTION AND MOVABLE GRIPPING PIECE — S5C

DETACH MOVABLE GRIPPING PIECE FROM SHEATH — S5D

END

TREATMENT TOOL, TREATMENT TOOL ASSEMBLING METHOD, AND TREATMENT TOOL DISASSEMBLING METHOD

CROSS-REFERENCE TO RELATED APPLICATION

This application is a continuation of International Application No. PCT/JP2020/018469, filed on May 1, 2020, the entire contents of which are incorporated herein by reference.

BACKGROUND

1. Technical Field

The present disclosure relates to a treatment tool, a treatment tool assembling method, and a treatment tool disassembling method.

2. Related Art

In the related art, there is a treatment tool for treating a treatment target site in a living tissue (hereinafter, described as a target site.

The treatment tool includes an outer pipe being a tubular elongated member, and a jaw pivotally attached to the outer pipe at a distal end of the outer pipe. The jaw pivots with respect to the outer pipe to grip the target site between the jaw and a distal end portion of a blade inserted into the outer pipe to transmit ultrasound vibration from the proximal end toward the distal end.

SUMMARY

In some embodiments, a treatment tool includes: a sheath extending along a longitudinal axis; a fixed gripping piece protruding from a distal end of the sheath; a movable gripping piece that is movably attached to either the sheath or the fixed gripping piece, the movable gripping piece being configured to grip a living tissue between the movable gripping piece and the fixed gripping piece; and a movement restricting portion configured to allow movement of the movable gripping piece in a first range and restrict movement of the movable gripping piece in a second range different from the first range. The movable gripping piece is attachable to and detachable from either the sheath or the fixed gripping piece at a movement position within the second range.

In some embodiments, a treatment tool assembling method includes: attaching a movable gripping piece to a distal end of a sheath to be movable; and inserting a vibration transmitting portion into the sheath, the vibration transmitting portion being configured to transmit ultrasound vibration. The vibration transmitting portion is configured to allow movement of the movable gripping piece in a first range and restrict movement of the movable gripping piece in a second range different from the first range, the movable gripping piece is attachable to and detachable from the sheath at a movement position within the second range, and the attaching includes attaching the movable gripping piece to the distal end of the sheath in a posture of the movable gripping piece being located at a movement position within the second range.

In some embodiments, a treatment tool disassembling method includes: extracting a vibration transmitting portion from inside a sheath, the vibration transmitting portion being configured to transmit ultrasound vibration; and detaching a movable gripping piece from the sheath, the movable gripping piece having been movably attached to a distal end of the sheath. The vibration transmitting portion is configured to allow movement of the movable gripping piece in a first range and restrict movement of the movable gripping piece in a second range different from the first range, the movable gripping piece is attachable to and detachable from the sheath at a movement position within the second range, and the detaching is performed in a state where the movable gripping piece is located at a movement position within the second range after the restriction of the movement of the movable gripping piece in the second range by the vibration transmitting portion is released in the extracting.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 29 is a flowchart illustrating a treatment tool assembling method;

FIG. 30 is a flowchart illustrating a treatment tool disassembling method;

DETAILED DESCRIPTION

Figure 1:
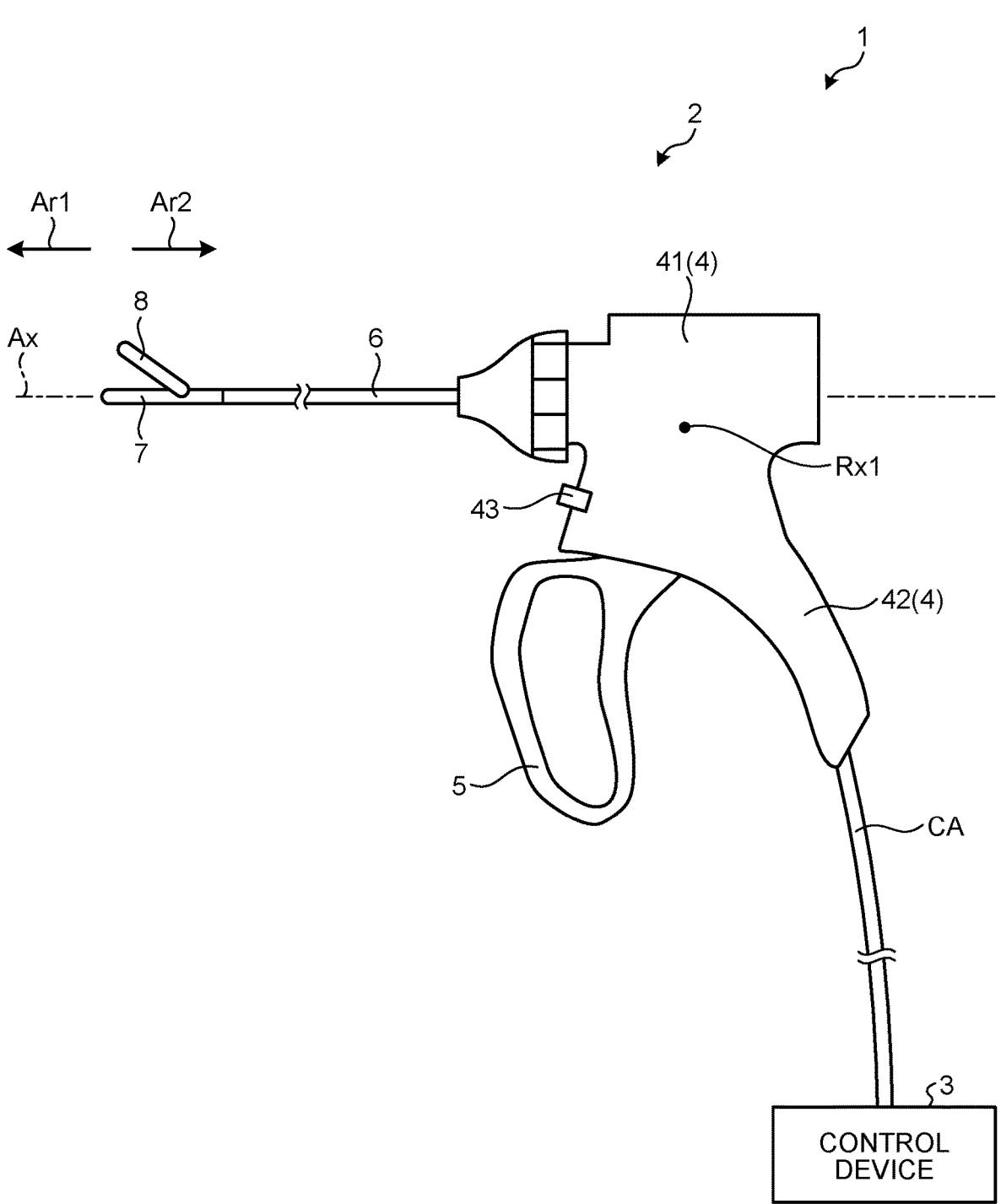
FIG. 1 is a view illustrating a treatment system according to an exemplary embodiment.

Hereinafter, a mode (hereinafter, "embodiment") for carrying out the disclosure will be described with reference to the accompanying drawings. Note that the disclosure is not limited to embodiments described below. In the drawings, same reference signs are attached to the same components.
Schematic Configuration of Treatment System FIG. 1 is a view illustrating a treatment system 1 according to an exemplary embodiment.

The treatment system 1 applies treatment energy to a site as a treatment target (hereinafter, referred to as a target site) in a living tissue, and thereby achieves treatment of the target site. In the present embodiment, thermal energy and high-frequency energy are employed as the treatment energy. In addition, the term treatment includes coagulation or incision of a target site. As illustrated in FIG. 1, the treatment system 1 includes a treatment tool 2 and a control device 3.
Configuration of Treatment Tool FIGS. 2 and 3 are views illustrating a distal end portion of the treatment tool 2. Specifically, FIG. 2 is a perspective view illustrating a distal end portion of the treatment tool 2. FIG. 3 is a cross-sectional view of the distal end portion of the treatment tool 2 taken along a plane including a longitudinal axis Ax of a sheath 6.

Hereinafter, for convenience of description, one side along the longitudinal axis (central axis) Ax of the sheath 6 is referred to as a distal end side Ar1, while the other side is referred to as a proximal end side Ar2.

Figure 2:
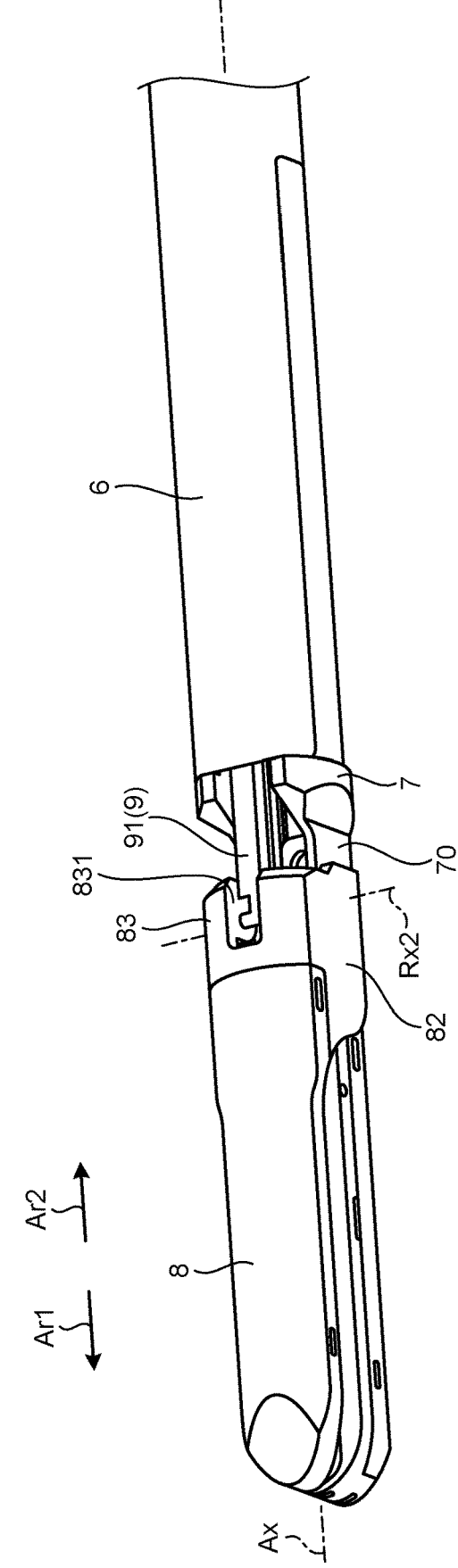
FIG. 2 is a view illustrating a distal end portion of a treatment tool.
Figure 3:
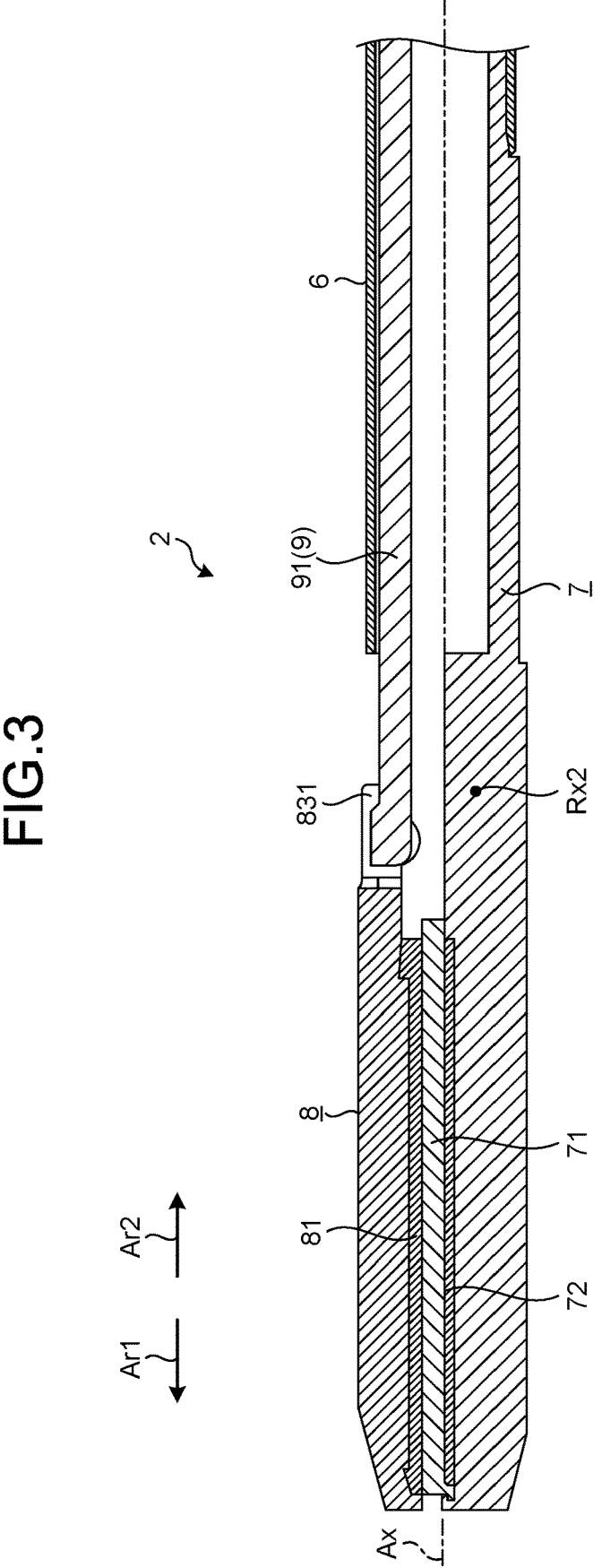
FIG. 3 is a view illustrating a distal end portion of a treatment tool.

As illustrated in FIGS. 1 to 3, the treatment tool 2 includes a housing 4 (FIG. 1), a movable handle 5 (FIG. 1), the sheath 6, first and second gripping pieces 7 and 8, and an open-close mechanism 9 (FIGS. 2 and 3).

The housing 4 supports the entire treatment tool 2. As illustrated in FIG. 1, the housing 4 includes: a housing body 41 being a substantially cylindrical body coaxial with the longitudinal axis Ax; and a fixed handle 42 extending downward in FIG. 1 from the housing body 41 and configured to be gripped by an operator.

As illustrated in FIG. 1, on a side surface of the housing 4 on the distal end side Ar1, there is provided a switch 43 in a state of being exposed to the outside. The switch 43 receives an output start operation by the operator. The output start operation is an operation of pressing the switch 43, and is an operation of starting application of treatment energy to a target site. The switch 43 then outputs an operation signal corresponding to the output start operation to the control device 3 via an electric cable CA (FIG. 1).

The movable handle 5 is pivotally and pivotably supported to the housing 4 so as to be pivotable about a first pivot shaft Rx1 orthogonal to the direction of the sheet surface of FIG. 1. The movable handle 5 receives a closing operation and an opening operation by the operator. The closing operation is an operation of pivoting the movable handle 5 about the first pivot shaft Rx1 in a direction approaching the fixed handle 42. The opening operation is an operation of pivoting the movable handle 5 about the first pivot shaft Rx1 in a direction away from the fixed handle 42.

The sheath 6 has a substantially cylindrical shape as a whole. An end of the sheath 6 on the proximal end side Ar2 is inserted into the housing 4. As illustrated in FIGS. 1 to 3, the first and second gripping pieces 7 and 8 are provided at the end of the sheath 6 on the distal end side Ar1.

The first gripping piece 7 has an elongated shape extending along the longitudinal axis Ax. In addition, the end of the first gripping piece 7 on the proximal end side Ar2 is fixed to the sheath 6 as illustrated in FIG. 2 or 3. That is, the first gripping piece 7 corresponds to a fixed gripping piece.

As illustrated in FIG. 3, the first gripping piece 7 includes a first electrode 71 and a heater 72 at an end on the distal end side Ar1 facing the second gripping piece 8.

The first electrode 71 is formed of a conductive material having high thermal conductivity such as copper, and has an elongated shape extending along the longitudinal axis Ax. The first electrode 71 provided in the first gripping piece 7 is in a state of being exposed to the outside.

The heater 72 provided in the first gripping piece 7 is in a state of being hidden inside by the first electrode 71. When activated by electric power supply, the heater 72 generates heat and heats the first electrode 71. Examples of the heater 72 include a sheet heater including a conductive pattern made on a substrate formed of polyimide or the like, a ceramic heater including a conductive pattern made on a ceramic substrate formed of aluminum nitride or the like, and other printed heaters.

The second gripping piece 8 has an elongated shape extending along the longitudinal axis Ax. An end of the second gripping piece 8 on the proximal end side Ar2 is pivotally supported on the first gripping piece 7 so as to be pivotable about a second pivot shaft Rx2 (FIGS. 2 and 3). Pivot movement of the second gripping piece 8 about the second pivot shaft Rx2 allows the second gripping piece 8 to perform open-close operation with respect to the first gripping piece 7, making it possible to grip the target site between the first and second gripping pieces 7 and 8. That is, the second gripping piece 8 corresponds to a movable gripping piece.

The second gripping piece 8 includes a second electrode 81 (FIG. 3), which is formed of a conductive material and provided at a position facing the first electrode 71, in a state of being exposed to the outside.

The attachment structure used to attach the second gripping piece 8 to the first gripping piece 7 will be described below in "Attachment structure used to attach second gripping piece to first gripping piece".

The open-close mechanism 9 is a mechanism that opens and closes the second gripping piece 8 with respect to the first gripping piece 7. As illustrated in FIG. 2 or 3, the open-close mechanism 9 includes a drive portion 91.

The drive portion 91 is an elongated member extending along the longitudinal axis Ax, and configured to be inserted into the sheath 6. Furthermore, an end of the drive portion 91 on the distal end side Ar1 is engaged with the second gripping piece 8.

The engagement structure between the second gripping piece 8 and the drive portion 91 will be described in "Engagement structure between second gripping piece and drive portion" described below.

The drive portion 91 operates as described below according to the operation of the movable handle 5 by the operator.

According to the closing operation of the movable handle 5 by the operator, the drive portion 91 receives a pressing force (driving force for gripping the target site between the first and second gripping pieces 7 and 8) toward the distal end side Ar1. The pressing force allows the drive portion 91 to move toward the distal end side Ar1 along the longitudinal axis Ax. The drive portion 91 then applies the driving force to the second gripping piece 8. This allows the second gripping piece 8 to pivot about the second pivot shaft Rx2 in a direction approaching the first gripping piece 7 (closing direction).

On the other hand, when the operator performs an opening operation on the movable handle 5, the drive portion 91 operates in a direction opposite to the above direction. This allows the second gripping piece 8 to pivot about the second pivot shaft Rx2 in a direction away from the first gripping piece 7 (opening direction).

As described above, the second gripping piece 8 opens and closes against the first gripping piece 7 according to the operation of the movable handle 5 by the operator.

Configuration of Control Device

The treatment tool 2 is detachably connected to the control device 3 by an electric cable CA. According to the operation signal input from the switch 43 via the electric cable CA, the control device 3 integrally controls the operation of the treatment tool 2 as described below.

The control device 3 supplies high-frequency power between the first and second electrodes 71 and 81 via the electric cable CA. This allows a high-frequency current to flow through the target site gripped between the first and second gripping pieces 7 and 8 (first and second electrodes 71 and 81). In other words, high-frequency energy is applied from the first and second electrodes 71 and 81 to the target site.

The control device 3 supplies power to the heater 72 via the electric cable CA. This causes the heater 72 to generate heat. The heat of the heater 72 is transferred to the target site gripped between the first and second gripping pieces 7 and 8 (first and second electrodes 71 and 81) through the first electrode 71. In other words, thermal energy is applied from the first electrode 71 to the target site.

Attachment Structure Used to Attach Second Gripping Piece to First Gripping Piece Next, an attachment structure used for attaching the second gripping piece 8 to the first gripping piece 7 will be described.

Figure 4:
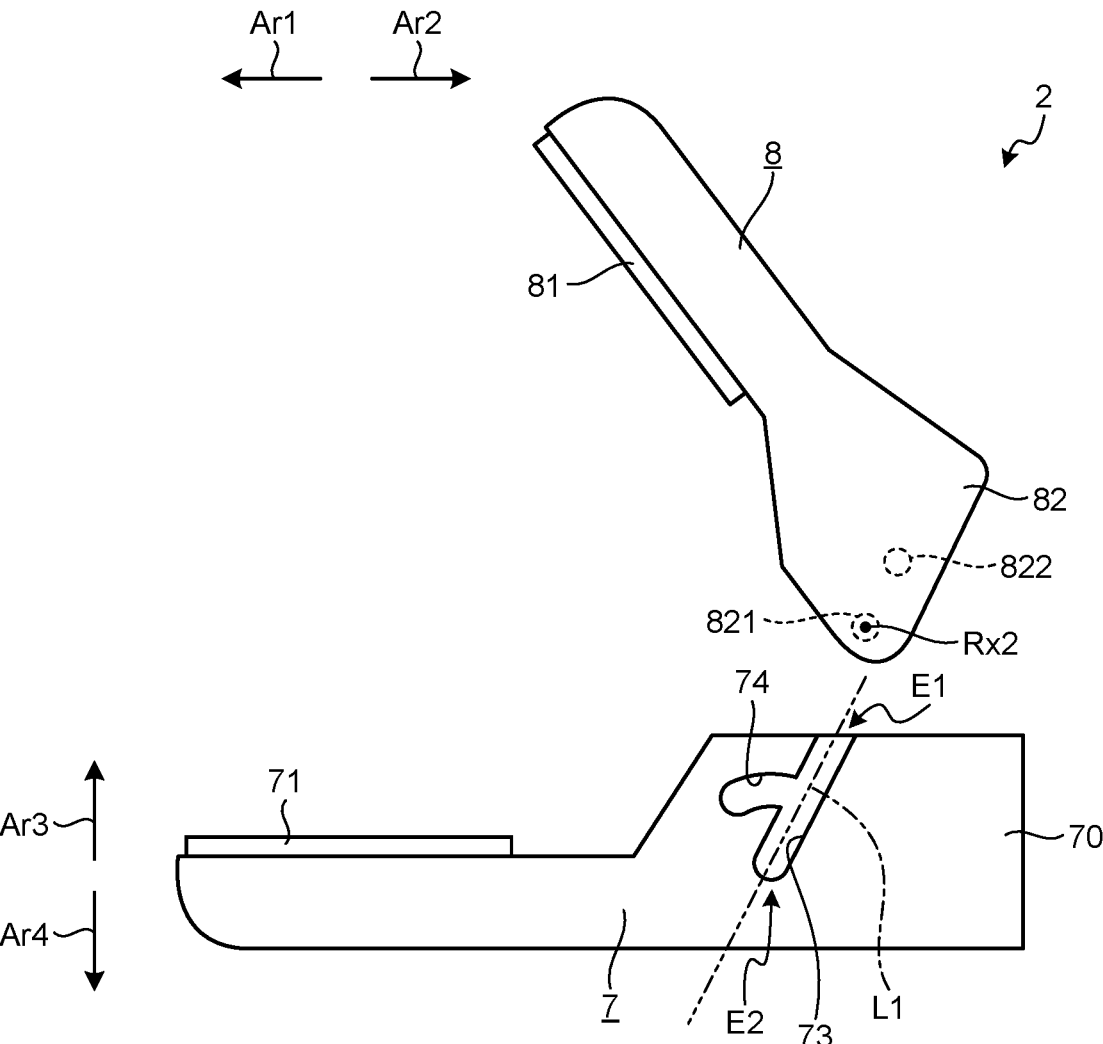
FIG. 4 is a view illustrating an attachment structure used to attach a second gripping piece to a first gripping piece.
Figure 5:
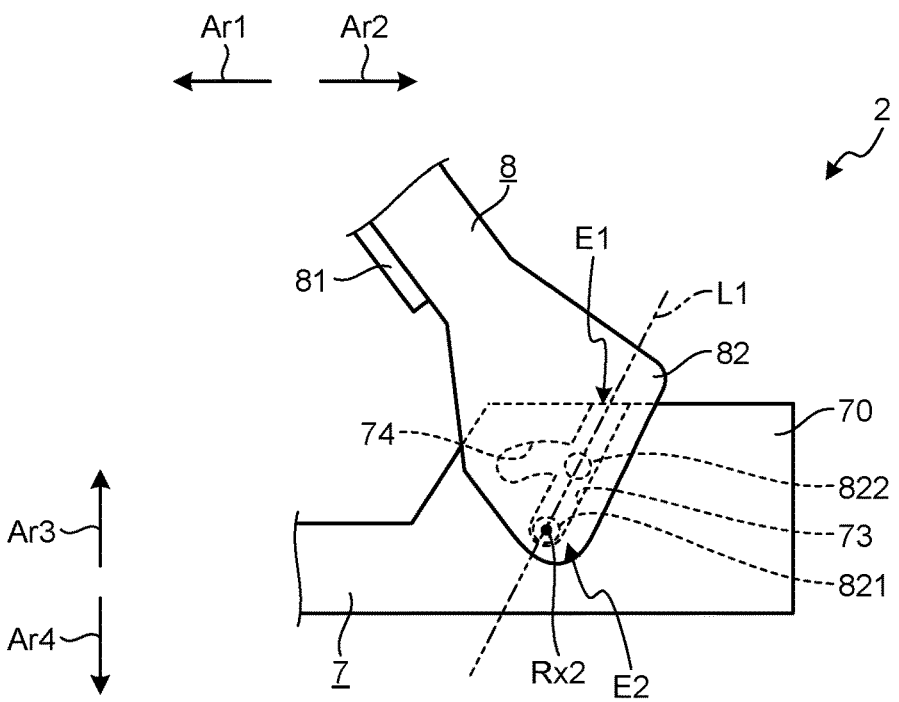
FIG. 5 is a view illustrating an attachment structure used to attach a second gripping piece to a first gripping piece.
Figure 6:
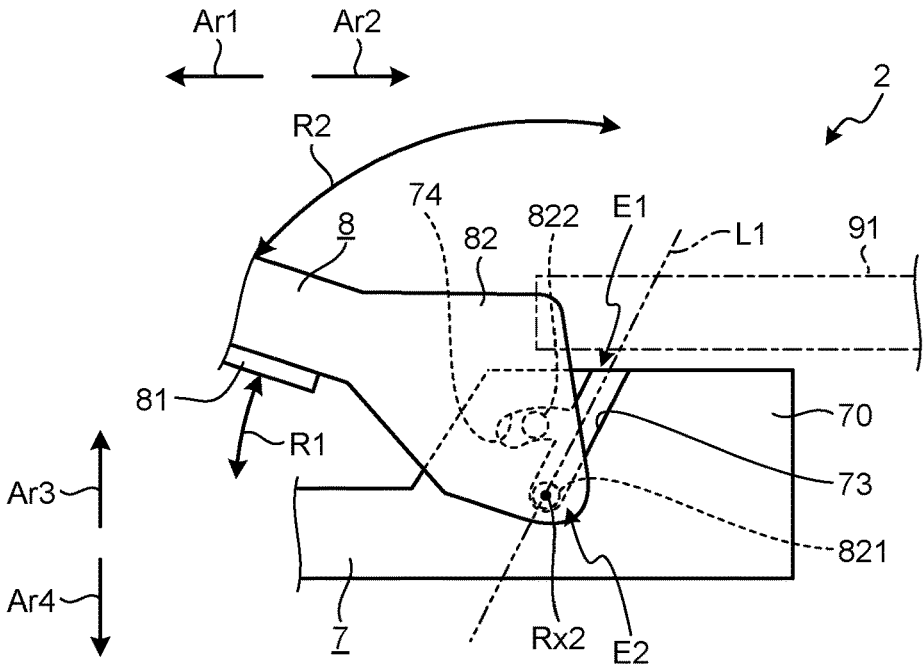
FIG. 6 is a view illustrating an attachment structure used to attach a second gripping piece to a first gripping piece.

FIGS. 4 to 6 are views illustrating an attachment structure used to attach the second gripping piece 8 to the first gripping piece 7. Specifically, FIGS. 4 to 6 are views of the first and second gripping pieces 7 and 8 along the second pivot shaft Rx2.

In the following, for convenience of description, in the direction in which the first and second gripping pieces 7 and 8 (first and second electrodes 71 and 81) face each other, that is, a facing direction (or vertical direction in FIGS. 4 to 6), the upper side (side on which the second gripping piece 8 (second electrode 81) is disposed) in FIGS. 4 to 6 is referred to as an upper side Ar3. In the facing direction in FIGS. 4 to 6, a lower side (side on which the first gripping piece 7 (the first electrode 71) is disposed) is referred to as a lower side Ar4.

The end of the second gripping piece 8 on the proximal end side Ar2 includes a pair of second connectors 82 and a base 83 as illustrated in FIG. 2.

Each of the pair of second connectors 82 is formed of a plate member intersecting the second pivot shaft Rx2, and faces each other. The pair of second connectors 82 has shapes that are symmetrical to each other with respect to a plane parallel to the sheet surface of FIGS. 4 to 6.

The base 83 is formed of a plate member substantially parallel to the second pivot shaft Rx2, and connects edges of the upper side Ar3 of the pair of second connectors 82.

The second gripping piece 8 is attached to the first gripping piece 7 in a state where a part of the first gripping piece 7 is housed inside a U-shaped cross section formed by the pair of second connectors 82 and the base 83.

On an inner surface of the second connector 82 (surface facing the other second connector 82), a pivot shaft 821 and a guide pin 822 are provided (FIGS. 4 to 6).

The pivot shaft 821 has a cylindrical shape protruding along the second pivot shaft Rx2. The pivot shaft 821 functions as a pivot center of the second gripping piece 8. That is, the second pivot shaft Rx2 corresponds to a central axis.

The guide pin 822 is provided at a position close to the pivot shaft 821 and has the same shape as the pivot shaft 821. The guide pin 822 guides the pivot operation of the second gripping piece 8.

The first gripping piece 7 is provided with a pair of first connectors 70 (FIGS. 2 and 4 to 6) facing the pair of second connectors 82.

Similarly to the second connector 82, each of the pair of first connectors 70 is formed of a plate member intersecting the second pivot shaft Rx2, and faces each other. The pair of first connectors 70 has shapes that are symmetrical to each other with respect to a plane parallel to the sheet surface of FIGS. 4 to 6.

An outer surface of first connector 70 (surface spaced apart from the other first connector 70, surface facing the second connector 82) is provided with a bearing 73 and an arc portion 74 (FIGS. 4 to 6).

The bearing 73 extends along a first straight line L1 (FIGS. 4 to 6) intersecting the second pivot shaft Rx2 from an outer edge of the first connector 70 (hereinafter, referred to as a starting end E1 (FIGS. 4 to 6)) on the upper side Ar3. The bearing 73 allows the pivot shaft 821 and the guide pin 822 to be inserted along the first straight line L1 from the starting end E1. In the present embodiment, the first straight line L1 is a straight line inclined onto the distal end side Ar1 toward the lower side Ar4 when viewed from a direction along the second pivot shaft Rx2. In addition, the bearing 73 is constituted by a groove recessed in a thickness direction of the plate member in the first connector 70 on the outer surface of the first connector 70. The bearing 73 pivotally and pivotably supports the pivot shaft 821 (second gripping piece 8) at a terminating end E2 (FIGS. 4 to 6) of the lower side Ar4.

The arc portion 74 is formed of a groove similarly to the bearing 73, and communicates with the bearing 73. In addition, the arc portion 74 extends from a communicating position with the bearing 73 toward the distal end side Ar1 in an arc shape centered on the second pivot shaft Rx2 located at the terminating end E2 of the bearing 73 and having a radius of a distance between the pivot shaft 821 and the guide pin 822. The guide pin 822 is inserted into the arc portion 74 in accordance with the pivot operation of the second gripping piece 8.

Engagement Structure Between Second Gripping Piece and Drive Portion

Next, an engagement structure between the second gripping piece 8 and the drive portion 91 will be described.

Figure 7:
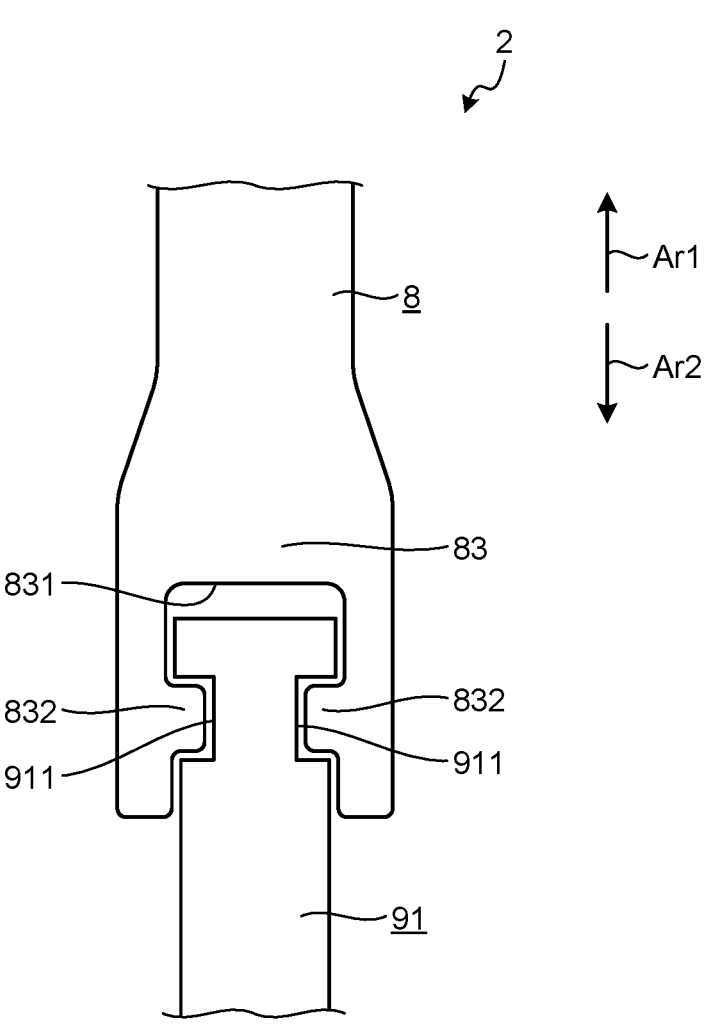
FIG. 7 is a view illustrating an engagement structure between a second gripping piece and a drive portion.

FIG. 7 is a view illustrating an engagement structure between the second gripping piece 8 and the drive portion 91. Specifically, FIG. 7 is a view illustrating the engagement structure between the second gripping piece 8 and the drive portion 91 as seen from the upper side Ar3.

The base 83 has a cutout portion 831 (FIGS. 2 and 7) cut out from the proximal end toward the distal end side Ar1 at a central portion in the direction along the second pivot shaft Rx2.

As illustrated in FIG. 7, on inner wall surfaces of the cutout portion 831 facing each other along the second pivot shaft Rx2, engagement pins 832 are provided.

These engagement pins 832 each have a cylindrical shape protruding in directions approaching each other along the second pivot shaft Rx2.

On the other hand, an end of the drive portion 91 on the distal end side Ar1 is provided with engagement grooves 911 (FIG. 7) respectively extending in directions (directions orthogonal to the sheet surface of FIG. 7) orthogonal to each of the protruding direction of the engagement pin 832 and the longitudinal axis Ax, each of the engagement grooves 911 configured to be engaged with each of the engagement pins 832.

When the drive portion 91 moves along the longitudinal axis Ax in a state where the engagement pin 832 and the engagement groove 911 are engaged with each other, the second gripping piece 8 performs open-close operation with respect to the first gripping piece 7 about the second pivot shaft Rx2.

Treatment Tool Assembling Method

Next, a method of assembling the treatment tool 2 will be described.

Figure 8:
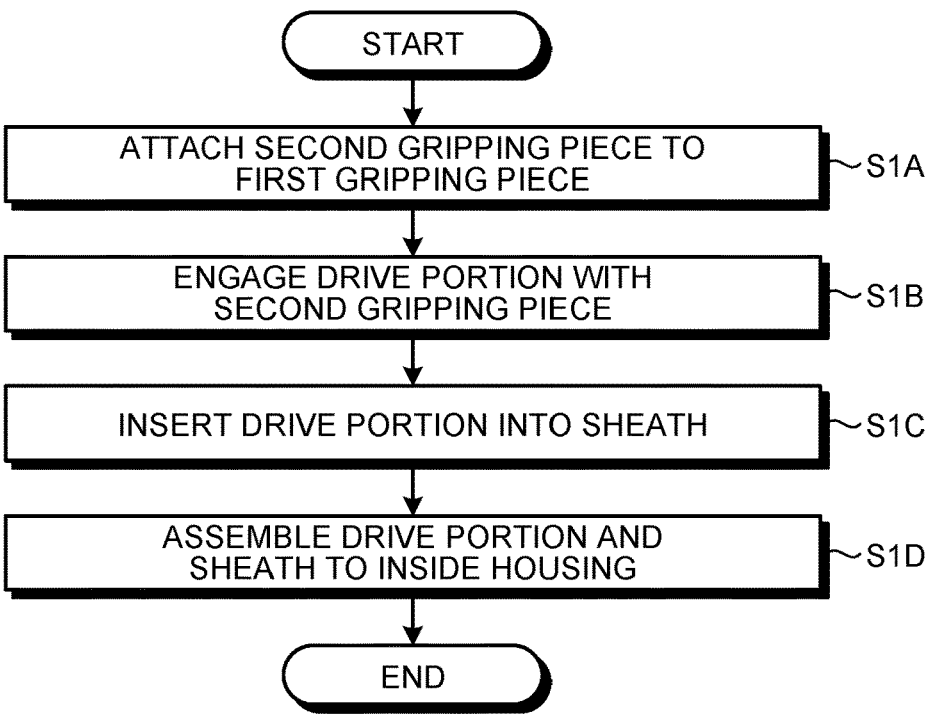
FIG. 8 is a flowchart illustrating a treatment tool assembling method.

FIG. 8 is a flowchart illustrating a method of assembling the treatment tool 2.

First, as described below, a worker attaches the second gripping piece 8 to the first gripping piece 7 (step S1A).

That is, as illustrated in FIG. 4, when viewed in the direction along the second pivot shaft Rx2, the worker sets the second gripping piece 8 to be in a posture in which a straight line connecting the pivot shaft 821 and the guide pin 822 is parallel to the first straight line L1. Subsequently, as illustrated in FIGS. 4 and 5, the worker inserts the pivot shaft 821 and the guide pin 822 into the bearing 73 from the starting end E1 of the bearing 73 while maintaining the posture. The posture of the second gripping piece 8 illustrated in FIGS. 4 and 5 is a posture in which the distal end of the second gripping piece 8 is located on the upper side Ar3 with respect to the second pivot shaft Rx2.

With the above step S1A, the second gripping piece 8 is attached to the first gripping piece 7 in a state where the pair of first connectors 70 is housed inside the U-shaped cross section formed by the pair of second connectors 82 and the base 83.

After step S1A, the worker engages the drive portion 91 with the second gripping piece 8 as described below (step S1B).

That is, the worker positions the end of the drive portion 91 on the distal end side Ar1 onto the upper side Ar3 of the second gripping piece 8. The worker then moves the end of the drive portion 91 on the distal end side Ar1 to the lower side Ar4, and inserts the pair of engagement pins 832 into the pair of engagement grooves 911. This allows the drive portion 91 to be engaged with the second gripping piece 8 as illustrated in FIG. 8.

After step S1B, the worker inserts the drive portion 91 into the sheath 6 from the proximal end side Ar2 of the sheath 6 (step S1C).

After step S1C, the worker assembles the ends of the drive portion 91 and the sheath 6 on the proximal end side Ar2 into the housing 4 (step S1D). This allows the drive portion 91 to be disposed at the position illustrated in FIG. 6. Specifically, the position illustrated in FIG. 6 is a limit position that allows the drive portion 91 to move toward the proximal end side Ar2 in a state where the operator has performed the opening operation on the movable handle 5. In the state where the drive portion 91 is located at the limit position, the second gripping piece 8 pivots in the closing direction about the second pivot shaft Rx2 from the state illustrated in FIG. 5, and the guide pin 822 is inserted into the arc portion 74.

That is, the drive portion 91 allows the pivot operation in a first range R1 (range illustrated in FIG. 6) in the closing direction of the second gripping piece 8 from the state illustrated in FIG. 6, and restricts the pivot operation in a second range R2 (range illustrated in FIG. 6) in the opening direction of the second gripping piece 8 from the state illustrated in FIG. 6. Accordingly, the drive portion 91 corresponds to a movement restricting portion.

In addition, the second gripping piece 8 is attachable to and detachable from the first gripping piece 7 at a pivoting position (position illustrated in FIG. 5) within the second range R2.

Furthermore, when the second gripping piece 8 is located at the attachment-detachment position (the position illustrated in FIG. 5) which is a pivoting position where the second gripping piece 8 is attachable to and detachable from the first gripping piece 7, the guide pin 822 is located in the bearing 73 and allows the movement of the pivot shaft 821 toward the starting end E1 in the bearing 73. That is, the second gripping piece 8 is detachable from the first gripping piece 7.

In contrast, when the second gripping piece 8 is located at the pivoting position within the first range R1 (the range illustrated in FIG. 6), the guide pin 822 is located in the arc portion 74 and restricts the movement of the pivot shaft 821 toward the starting end E1 in the bearing 73. That is, the second gripping piece 8 is not detachable from the first gripping piece 7.

Treatment Tool Disassembling Method

Next, a method of disassembling the treatment tool 2 will be described.

Figure 9:
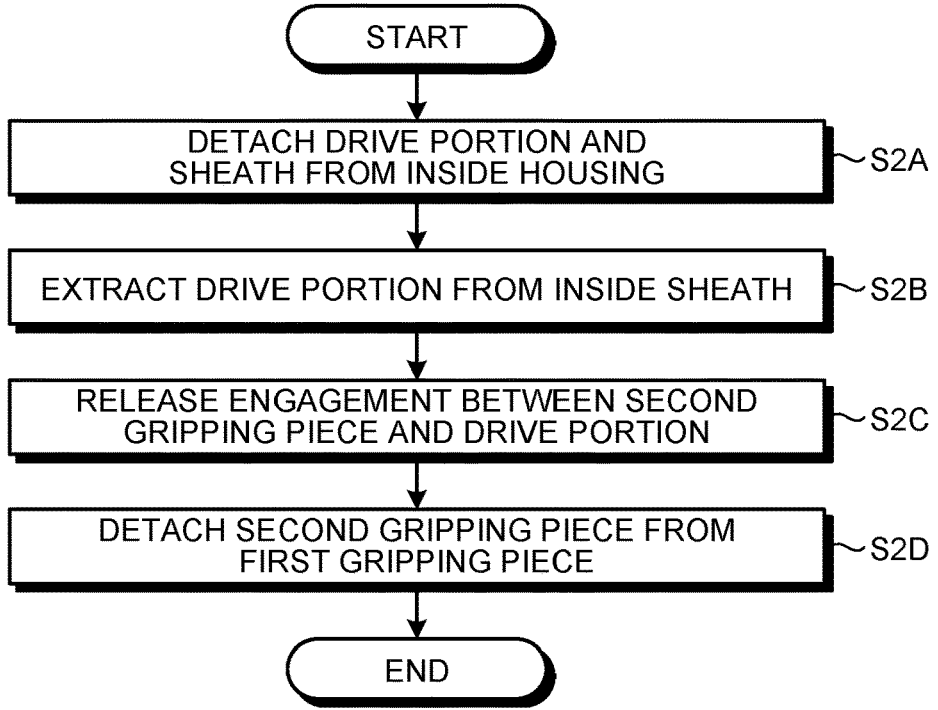
FIG. 9 is a flowchart illustrating a treatment tool disassembling method.

FIG. 9 is a flowchart illustrating a method of disassembling the treatment tool 2.

Note that, the method of disassembling the treatment tool 2 performs reverse of individual steps of the above-described method of assembling the treatment tool 2. Therefore, the method of disassembling the treatment tool 2 will be briefly described below.

First, the worker detaches the end of the drive portion 91 and the sheath 6 on the proximal end side Ar2 from inside the housing 4 (step S2A).

After step S2A, the worker extracts the drive portion 91 from inside the sheath 6 (step S2B).

After step S2B, the worker releases the engagement between the second gripping piece 8 (engagement pin 832) and the drive portion 91 (engagement groove 911) (step S2C).

After step S2C, the worker positions the second gripping piece 8 at the attachment-detachment position (position illustrated in FIG. 5), and moves the pivot shaft 821 and the guide pin 822 toward the starting end E1 in the bearing 73, thereby detaching the second gripping piece 8 from the first gripping piece 7 (step S2D).

The treatment tool 2 described above may be disposed after each time of use, or may be repeatedly used a plurality of times. In the case of a plurality of times of use, for example, there is a need to perform remanufacturing by the reprocessing method illustrated in FIG. 10.

Reprocessing Method

Figure 10:
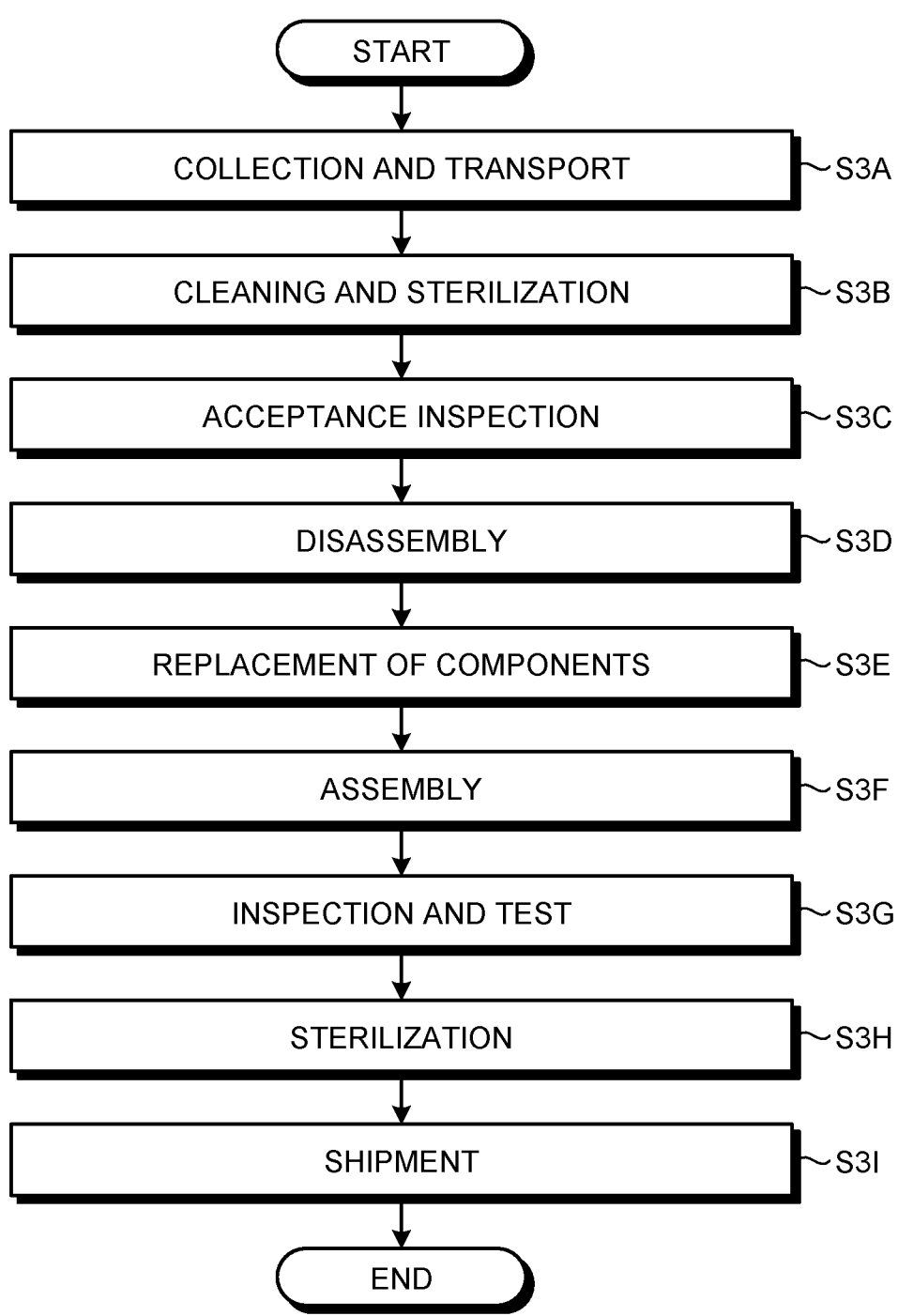
FIG. 10 is a flowchart illustrating a treatment tool reprocessing method.

FIG. 10 is a flowchart illustrating a reprocessing method.

First, the marketing authorization holder in charge of remanufacturing collects the used treatment tool 2 after being used for treatment and transports the used treatment tool 2 to a factory or the like (step S3A). At this time, the used treatment tool 2 is transported in a dedicated container in order to prevent contamination from the treatment tool 2.

After step S3A, the marketing authorization holder cleans and sterilizes the collected and transported used treatment tool 2 (step S3B), and performs an acceptance inspection to determine whether the used treatment tool 2 can be remanufactured (step S3C). For example, in the acceptance inspection, the used treatment tool 2 having a significant defect or having been used the number of times exceeding a remanufacturable limit is determined to be not remanufacturable.

After step S3C, the marketing authorization holder disassembles the used treatment tool 2 by the method of disassembling the treatment tool 2 described above (FIG. 9) (step S3D).

After step S3D, the marketing authorization holder performs a component replacement step (step S3E). For example, in the component replacement step, the first and second gripping pieces 7 and 8 worn by the treatment or to which dirt adheres are replaced with new components.

After step S3E, the marketing authorization holder reassembles each component by the above-described method of assembling the treatment tool 2 (FIG. 8) (step S3F), and performs inspection and test on the newly formed treatment tool 2 (step S3G). Here, regarding the inspection and test, verification is performed to verify that the newly formed treatment tool 2 has the same effectiveness and safety as the original product.

After step S3G, the marketing authorization holder packages the newly formed treatment tool 2, and then performs second sterilization (step S3H). For example, the sterilization uses a sterilization indicator such as a biological indicator (B.I.) to ensure the sterilization performance.

After step S3H, the marketing authorization holder ships the treatment tool 2 (step S3I).

Steps S3A to S3I described above are executed to achieve remanufacturing of the treatment tool 2.

According to the present embodiment, the following effects are obtained.

In the treatment tool 2 according to the present embodiment, the drive portion 91 allows pivot operation of the second gripping piece 8 in the first range R1 and restricts the pivot operation of the second gripping piece 8 in the second range R2. In addition, the second gripping piece 8 is attachable to and detachable from the first gripping piece 7 at a pivoting position (position illustrated in FIG. 5) within the second range R2.

Accordingly, since the treatment tool 2 of the present embodiment does not use the conventional welding in attaching the second gripping piece 8 to the first gripping piece 7, it is possible to facilitate assembly and disassembly. In addition, after the assembly of the treatment tool 2, the pivot operation of the second range R2 in the second gripping piece 8 is restricted by the drive portion 91, making it possible to use the treatment tool 2 reliably and safely. In particular, the second gripping piece 8 can be attached to and detached from the first gripping piece 7 only at the position illustrated in FIG. 5, which is the end of the second range R2. In other words, in the second range R2, there is a range (margin) that disables detachment of the second gripping piece 8 from the first gripping piece 7. Therefore, even when elastic deformation occurs in the first and second gripping pieces 7 and 8 at the time of using the treatment tool 2 or even when dimensional variations occur in the first and second gripping pieces 7 and 8, the assembled state can be stably maintained after the treatment tool 2 is assembled.

Furthermore, a conventionally used drive portion 91 is adopted as the movement restricting portion. This eliminates necessity to additionally provide the movement restricting portion, resulting in no increase in the number of parts.

In addition, the treatment tool 2 according to the present embodiment includes the guide pin 822 and the arc portion 74 in addition to the pivot shaft 821 and the bearing 73. This makes it possible to smoothly perform open-close operation of the second gripping piece 8 with respect to the first gripping piece 7 while having a structure that facilitates assembly and disassembly of the treatment tool 2.

Furthermore, in the treatment tool 2 according to the present embodiment, the bearing 73 is formed by a groove. Therefore, as compared with a case where the bearing 73 is formed as a through hole penetrating the front and back surfaces of the first connector 70, it is possible to avoid opening of the starting end E1, making it possible to properly support the pivot shaft 821 by the bearing 73. That is, it is possible to stably maintain the attached state of the second gripping piece 8 with respect to the first gripping piece 7.

Furthermore, in the treatment tool 2 according to the present embodiment, the second gripping piece 8 and the drive portion 91 are engaged with each other by the engagement pin 832 and the engagement groove 911. This eliminates necessity to use welding between the second gripping piece 8 and the drive portion 91 similarly to between the second gripping piece 8 and the first gripping piece 7. This makes it possible to facilitate assembly and disassembly of the treatment tool 2.

Next, another exemplary embodiment will be described.

In the following description, identical reference numerals are given to the components similar to those in the embodiment described above, and detailed description thereof will be omitted or simplified.

The present embodiment is different from the above-described embodiment in the structure of attaching the second gripping piece 8 to the first gripping piece 7.

Hereinafter, for convenience of description, the treatment tool 2 according to the present embodiment is referred to as a treatment tool 2A. In addition, the first gripping piece 7 according to the present embodiment will be referred to as a first gripping piece 7A. Furthermore, the second gripping piece 8 according to the present embodiment will be referred to as a second gripping piece 8A.

Figure 11:
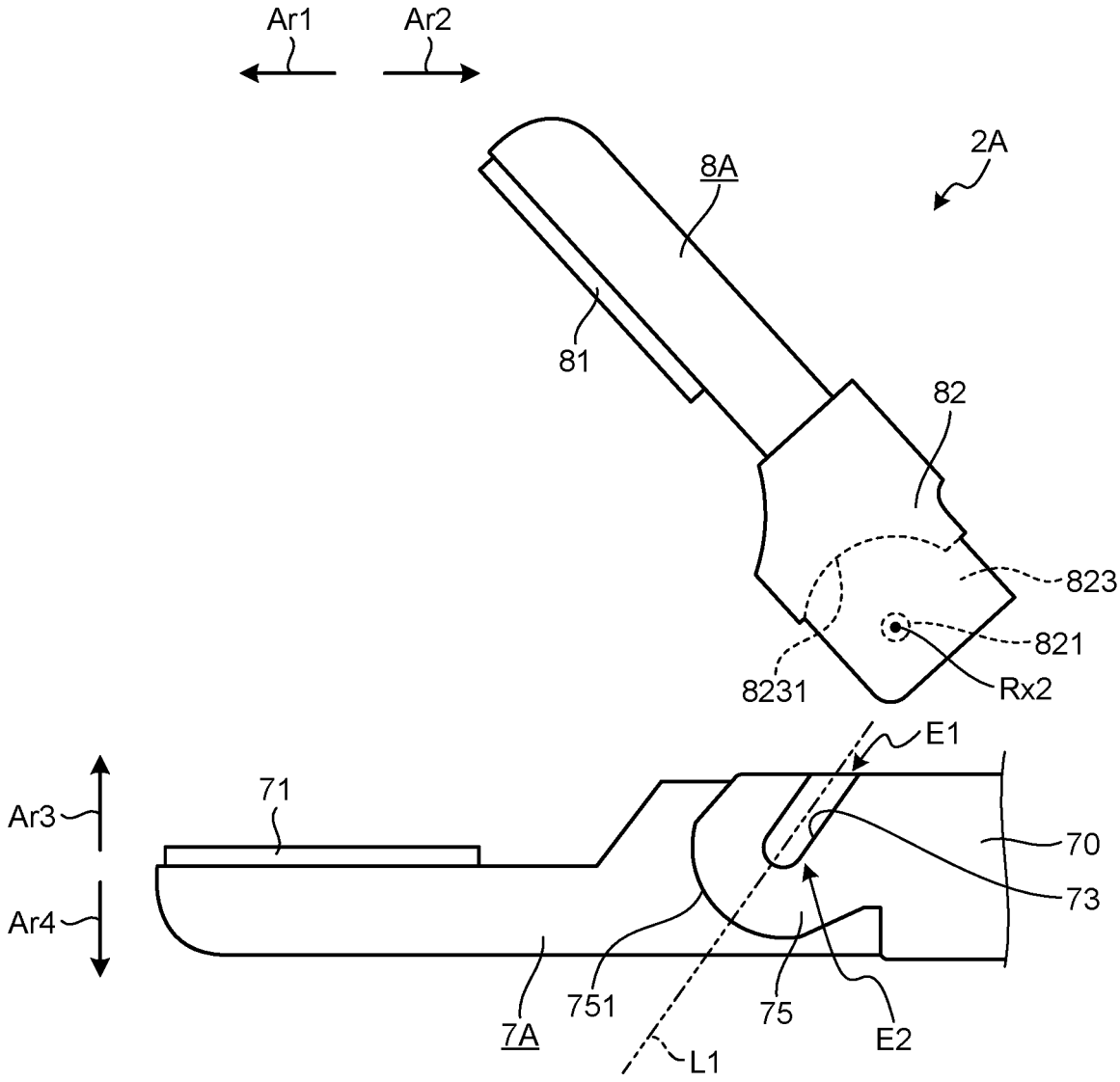
FIG. 11 is a view illustrating an attachment structure used to attach a second gripping piece to a first gripping piece according to an exemplary embodiment.
Figure 12:
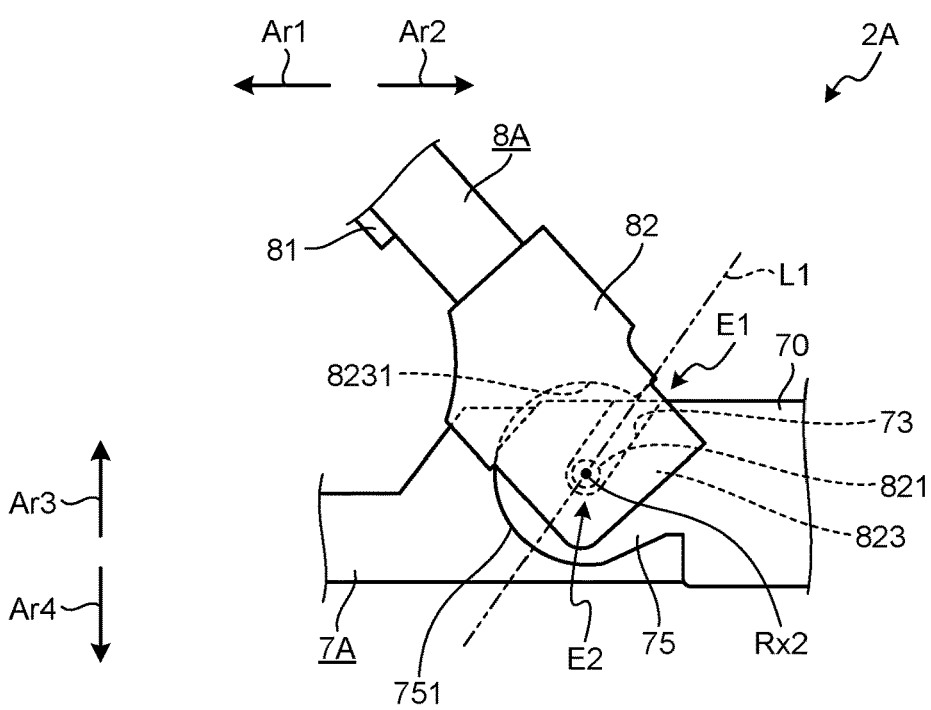
FIG. 12 is a view illustrating an attachment structure used to attach the second gripping piece to the first gripping piece according to an exemplary embodiment.
Figure 13:
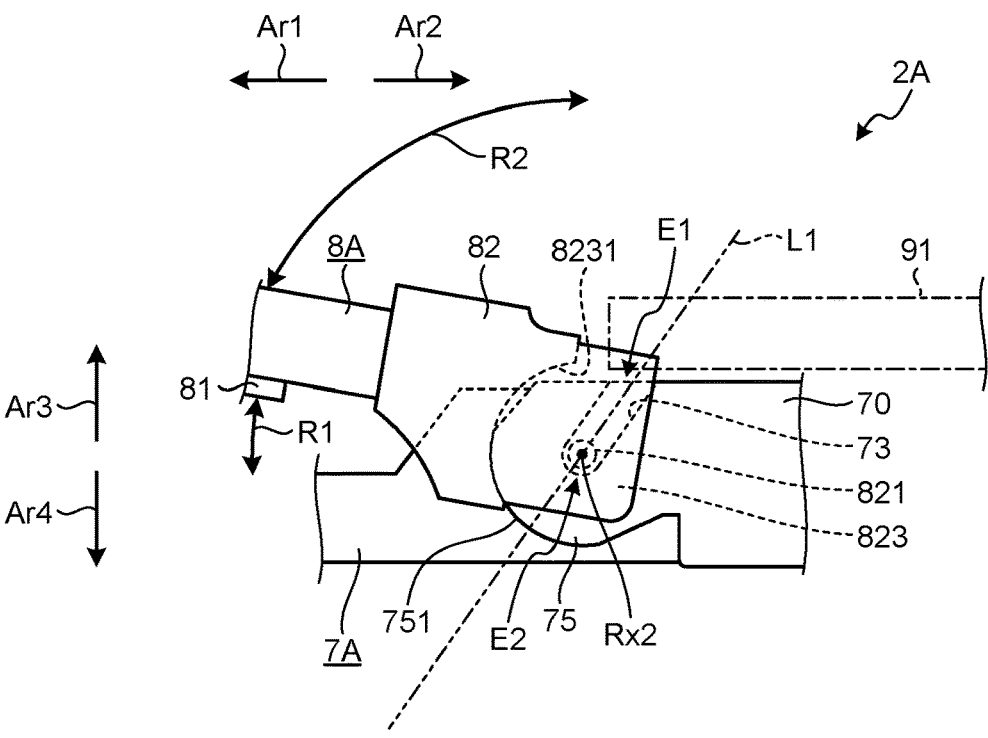
FIG. 13 is a view illustrating an attachment structure used to attach the second gripping piece to the first gripping piece according to an exemplary embodiment.

FIGS. 11 to 13 are views illustrating an attachment structure used to attach the second gripping piece 8A to the first gripping piece 7A. Specifically, FIGS. 11 to 13 are views of the first and second gripping pieces 7A and 8A along the second pivot shaft Rx2.

As compared with the first gripping piece 7 described in the above-described embodiment, the first gripping piece 7A includes an engagement protrusion 75 instead of the arc portion 74.

The engagement protrusion 75 is provided on an outer surface of the first connector 70 (a surface facing the second connector 82). Note that, also in the present embodiment, the pair of first connectors 70 has shapes that are symmetrical to each other with respect to a plane parallel to the sheet surface of FIGS. 11 to 13.

More specifically, on the outer surface of the first connector 70, the engagement protrusion 75 protrudes in the thickness direction of the plate member in the first connector 70. The bearing 73 is provided at the tip of the engagement protrusion 75. In addition, on the outer surface of the engagement protrusion 75, there is provided a first arc surface 751 having an arc shape and centered on the second pivot shaft Rx2 positioned at the terminating end E2 of the bearing 73. The first arc surface 751 is located on the terminating end E2 side and intersects the first straight line L1 when viewed in the direction along the second pivot shaft Rx2.

As compared with the second gripping piece 8 described in the above-described embodiment, the second gripping piece 8A includes an engagement recess 823 instead of the guide pin 822.

The engagement recess 823 is provided on an inner surface of the second connector 82 (a surface facing the other second connector 82). Note that, also in the present embodiment, the pair of second connectors 82 has shapes that are symmetrical to each other with respect to a plane parallel to the sheet surface of FIGS. 11 to 13.

More specifically, on the inner surface of the second connector 82, the engagement recess 823 is recessed in the thickness direction of the plate member in the second connector 82 so as to be capable of housing the engagement protrusion 75. The pivot shaft 821 is provided on the bottom surface of the engagement recess 823. In addition, on the inner side surface of the engagement recess 823, there is provided a second arc surface 8231 having an arc shape centered on the second pivot shaft Rx2.

In the method of assembling the treatment tool 2A according to the present embodiment, step S1A has a difference compared with step S1A in the method for assembling the treatment tool 2 described in the above embodiment (FIG. 8).

In step S1A according to the present embodiment, the worker attaches the second gripping piece 8A to the first gripping piece 7A as described below.

That is, as illustrated in FIG. 11, the worker sets the second gripping piece 8A in a posture in which the second arc surface 8231 faces the lower side Ar4 when viewed in a direction along the second pivot shaft Rx2. Subsequently, as illustrated in FIGS. 11 and 12, the worker inserts the pivot shaft 821 into the bearing 73 from the starting end E1 of the bearing 73 while maintaining the posture. With this operation, the engagement protrusion 75 is housed in the engagement recess 823. The posture of the second gripping piece 8A illustrated in FIGS. 11 and 12 is a posture in which the distal end of the second gripping piece 8A is located on the upper side Ar3 with respect to the second pivot shaft Rx2, similarly to the posture of the second gripping piece 8 described in the above embodiment illustrated in FIGS. 4 and 5.

With the above step S1A, the second gripping piece 8A is attached to the first gripping piece 7A in a state where the pair of first connectors 70 is housed inside the U-shaped cross section formed by the pair of second connectors 82 and the base 83.

When step S1D is completed, the drive portion 91 is positioned at the position illustrated in FIG. 13. Specifically, the position illustrated in FIG. 13 is a limit position that allows the drive portion 91 to move toward the proximal end side Ar2 in a state where the operator has performed the opening operation on the movable handle 5. In the state where the drive portion 91 is located at the limit position, the second gripping piece 8A pivots in the closing direction about the second pivot shaft Rx2 from the state illustrated in FIG. 12, and a part of the second arc surface 8231 faces a part of the first arc surface 751.

That is, the drive portion 91 allows the pivot operation in a first range R1 in the closing direction of the second gripping piece 8A from the state illustrated in FIG. 13, and restricts the pivot operation in a second range R2 in the opening direction of the second gripping piece 8A from the state illustrated in FIG. 13.

In addition, the second gripping piece 8A is attachable to and detachable from the first gripping piece 7A at a pivoting position (position illustrated in FIG. 12) within the second range R2.

Furthermore, the first and second arc surfaces 751 and 8231 do not face each other when the second gripping piece 8A is located at an attachment-detachment position (position illustrated in FIG. 12) being a pivoting position at which the second gripping piece 8A is attachable to and detachable from the first gripping piece 7A. Therefore, the engagement protrusion 75 and the engagement recess 823 allow the pivot shaft 821 to move toward the starting end E1 in the bearing 73. That is, the second gripping piece 8A is detachable from the first gripping piece 7A.

In contrast, when the second gripping piece 8A is located at a pivoting position within the first range R1, the first and second arc surfaces 751 and 8231 partially face each other. Therefore, the engagement protrusion 75 and the engagement recess 823 restricts the movement of the pivot shaft 821 toward the starting end E1 in the bearing 73. That is, the second gripping piece 8A is not detachable from the first gripping piece 7A.

Note that, the method of disassembling the treatment tool 2A performs reverse of individual steps of the above-described method of assembling the treatment tool 2A, and thus, description will be omitted.

With the present embodiment, effects similar to the effects of the above-described embodiment can be achieved.

Next, another exemplary embodiment will be described.

In the following description, identical reference numerals are given to the components similar to those in the exemplary embodiments described above, and detailed description thereof will be omitted or simplified.

The present embodiment is different from the above embodiment shown in FIGS. 1-10 in the structure for attaching the second gripping piece 8 to the first gripping piece 7.

Hereinafter, for convenience of description, the treatment tool 2 according to the present embodiment is referred to as a treatment tool 2B. In addition, the first gripping piece 7 according to the present embodiment will be referred to as a first gripping piece 7B. Furthermore, the second gripping piece 8 according to the present embodiment will be referred to as a second gripping piece 8B.

Figure 14:
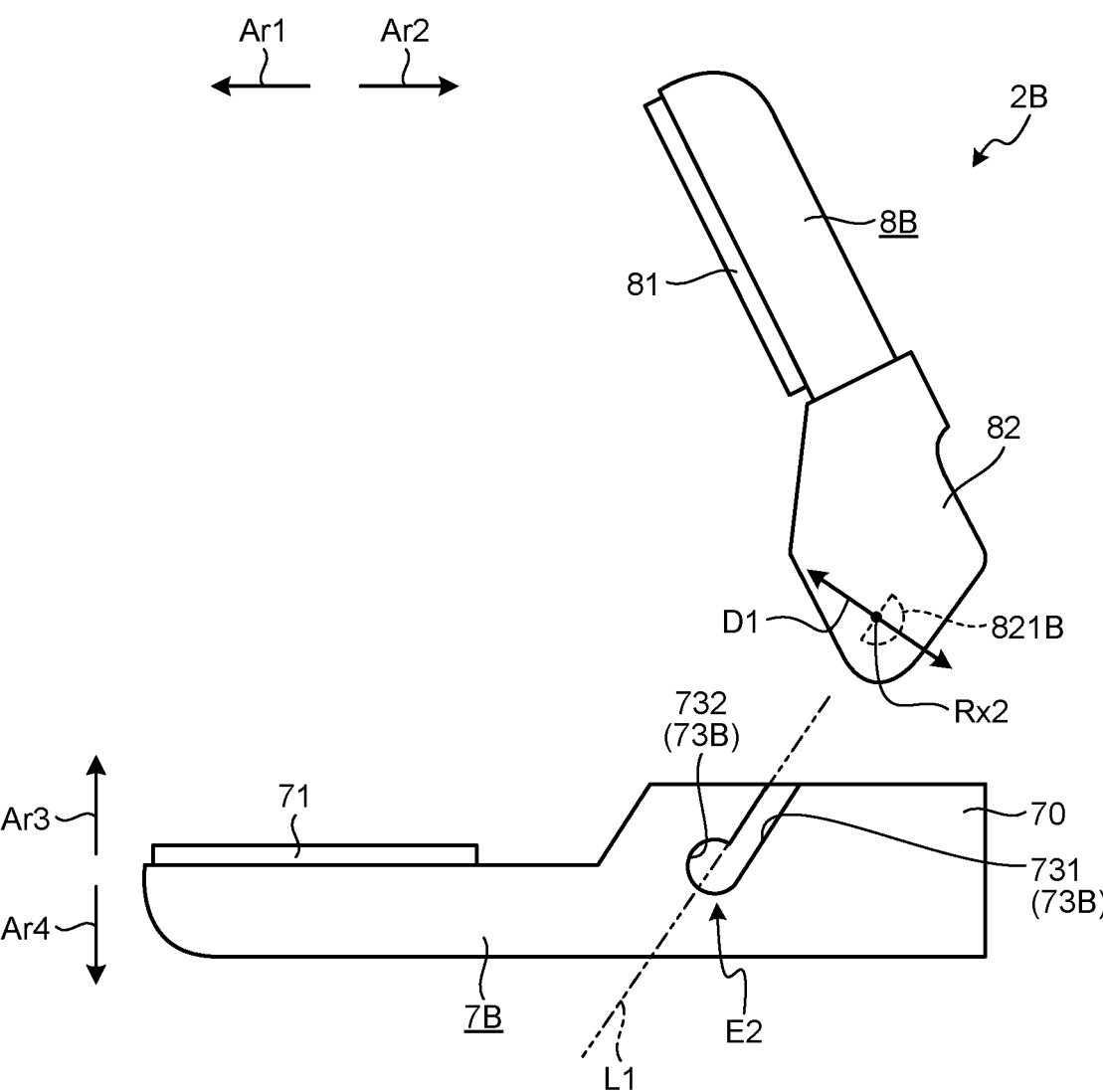
FIG. 14 is a view illustrating an attachment structure used to attach the second gripping piece to the first gripping piece according to an exemplary embodiment.
Figure 15:
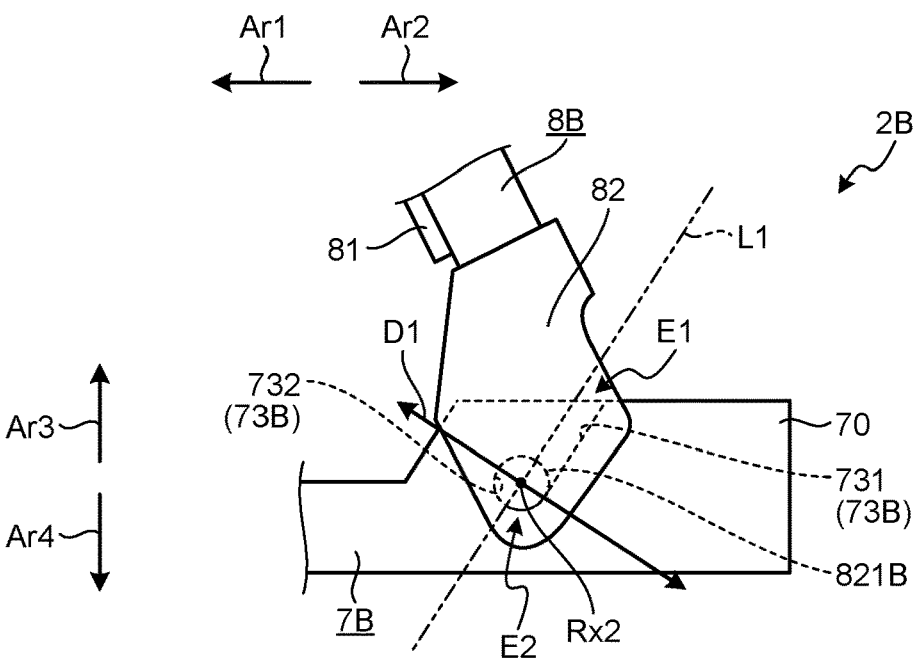
FIG. 15 is a view illustrating an attachment structure used to attach the second gripping piece to the first gripping piece according to an exemplary embodiment.
Figure 16:
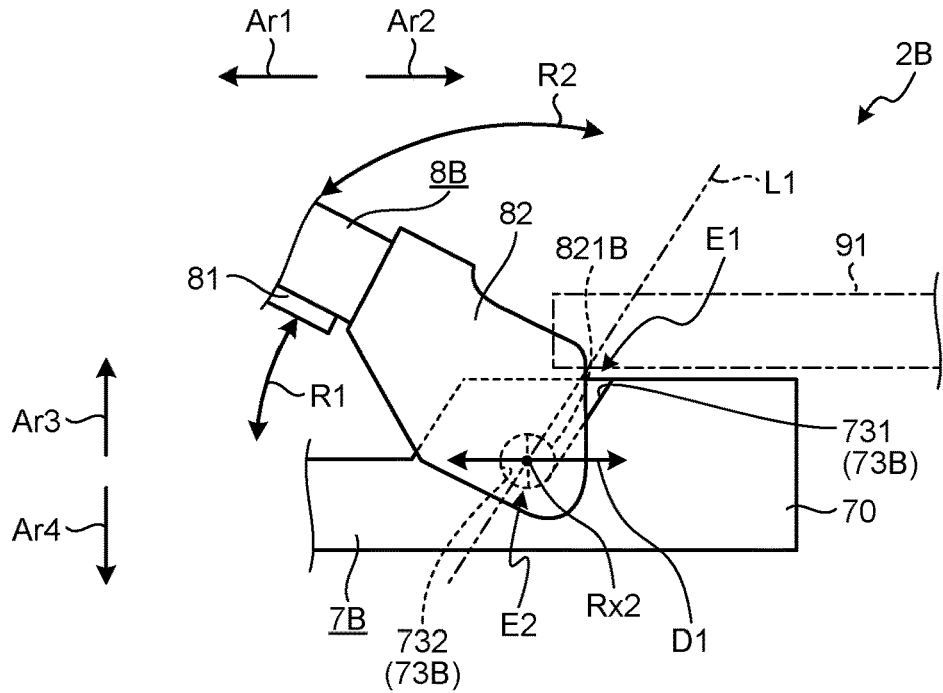
FIG. 16 is a view illustrating an attachment structure used to attach the second gripping piece to the first gripping piece according to an exemplary embodiment.

FIGS. 14 to 16 are views illustrating an attachment structure used to attach the second gripping piece 8B to the first gripping piece 7B. Specifically, FIGS. 14 to 16 are views of the first and second gripping pieces 7B and 8B along the second pivot shaft Rx2.

As compared with the first gripping piece 7 described in the above-described embodiment (FIGS. 1-10), the first gripping piece 7B has no arc portion 74 and has a bearing 73 having a shape different from the bearing 73 in the above embodiment. Hereinafter, for convenience of description, the bearing 73 according to the present embodiment will be referred to as a bearing 73B.

As compared with the second gripping piece 8 described in the above-described embodiment (FIGS. 1-10), the second gripping piece 8B has no guide pin 822 and has a pivot shaft 821 having a shape different from the pivot shaft 821 in the above-described embodiment. Hereinafter, for convenience of description, the pivot shaft 821 according to the present embodiment will be referred to as a pivot shaft 821B.

As illustrated in FIGS. 14 to 16, the bearing 73B includes an insertion portion 731 and a bearing body 732.

Similarly to the bearing 73 described in the above-described embodiment (FIGS. 1-10), the insertion portion 731 extends along the first straight line L1 intersecting the second pivot shaft Rx2 from the outer edge (hereinafter, it is described as a starting end E1) of the upper side Ar3 in the first connector 70. The insertion portion 731 allows the pivot shaft 821B to be inserted along the first straight line L1 from the starting end E1. In the present embodiment, similarly to the bearing 73, the insertion portion 731 is constituted by a groove recessed in a thickness direction of the plate member in the first connector 70 on the outer surface of the first connector 70.

Similarly to the insertion portion 731, the bearing body 732 is formed of a groove, and communicates with a terminating end E2 of the insertion portion 731 on the lower side Ar4. The bearing body 732 has a circular shape with a width dimension of the insertion portion 731 as a radius when viewed in a direction along the second pivot shaft Rx2. The bearing body 732 pivotally and pivotably supports the pivot shaft 821B (the second gripping piece 8B).

The pivot shaft 821B protrudes along the second pivot shaft Rx2, and has a semicircular cross section taken along a plane orthogonal to the second pivot shaft Rx2. In the present embodiment, the radius of the semicircular shape of the pivot shaft 821B is slightly smaller than the width dimension of the insertion portion 731.

Here, the direction orthogonal to the semicircular chord in the pivot shaft 821B corresponds to a first direction D1. That is, in the present embodiment, regarding the outer dimension of the pivot shaft 821B in a direction orthogonal to the second pivot shaft Rx2, an outer dimension in the first direction D1 (the radius of the semicircular shape in the pivot shaft 821B) is the smallest.

In the method of assembling the treatment tool 2B according to the present embodiment, step S1A has a difference compared with step S1A in the method for assembling the treatment tool 2 described in the above-described embodiment (see FIG. 8).

In step S1A according to the present embodiment, the worker attaches the second gripping piece 8B to the first gripping piece 7B as described below.

That is, as illustrated in FIG. 14, when viewed in the direction along the second pivot shaft Rx2, the worker sets the second gripping piece 8B in a posture in which the first direction D1 is orthogonal to the first straight line L1, in other words, a posture in which the chord of the semicircular shape in the pivot shaft 821B is parallel to the first straight line L1. Subsequently, as illustrated in FIGS. 14 and 15, the worker inserts the pivot shaft 821B into the bearing 73B from the starting end E1 of the insertion portion 731 while maintaining the posture. The posture of the second gripping piece 8B illustrated in FIGS. 14 and 15 is a posture in which the distal end of the second gripping piece 8B is located on the upper side Ar3 with respect to the second pivot shaft Rx2, similarly to the posture of the second gripping piece 8 described in the above-described embodiment illustrated in FIGS. 4 and 5.

With the above step S1A, the second gripping piece 8B is attached to the first gripping piece 7B in a state where the pair of first connectors 70 is housed inside the U-shaped cross section formed by the pair of second connectors 82 and the base 83.

When step S1D is completed, the drive portion 91 is positioned at the position illustrated in FIG. 16. Specifically, the position illustrated in FIG. 16 is a limit position that allows the drive portion 91 to move toward the proximal end side Ar2 in a state where the operator has performed the opening operation on the movable handle 5. In the state where the drive portion 91 is located at the limit position, the second gripping piece 8B pivots in the closing direction about the second pivot shaft Rx2 from the state illustrated in FIG. 15, and the chord of the semicircular shape in the pivot shaft 821B intersects the first straight line L1.

That is, the drive portion 91 allows the pivot operation in a first range R1 in the closing direction of the second gripping piece 8B from the state illustrated in FIG. 16, and restricts the pivot operation in a second range R2 in the opening direction of the second gripping piece 8B from the state illustrated in FIG. 16.

In addition, the second gripping piece 8B is attachable to and detachable from the first gripping piece 7B at a pivoting position (position illustrated in FIG. 15) within the second range R2.

Furthermore, when the second gripping piece 8B is located at the attachment-detachment position (the position illustrated in FIG. 15) which is the pivoting position where the second gripping piece 8B can be attached to and detached from the first gripping piece 7B, the pivot shaft 821B is allowed to move from the bearing body 732 to the insertion portion 731. That is, the second gripping piece 8B is detachable from the first gripping piece 7B.

In contrast, when the second gripping piece 8B is located at the pivoting position within the first range R1, because of interference with the inner wall surface of the insertion portion 731, the pivot shaft 821B is not allowed to move from the bearing body 732 to the insertion portion 731. That is, the second gripping piece 8B is not detachable from the first gripping piece 7B.

Note that, the method of disassembling the treatment tool 2B performs reverse of individual steps of the above-described method of assembling the treatment tool 2B, and thus, description will be omitted.

With the present embodiment, effects similar to the effects of the above-described embodiment (FIGS. 1-10) can be achieved.

Next, another exemplary embodiment will be described.

In the following description, identical reference numerals are given to the components similar to those in embodiments described above, and detailed description thereof will be omitted or simplified.

In the above-described embodiment shown in FIGS. 14-16, the drive portion 91 is adopted as the movement restricting portion.

In contrast, in the present embodiment, the sheath 6 is adopted as the movement restricting portion.

Hereinafter, for convenience of description, the treatment tool 2 according to the present embodiment is referred to as a treatment tool 2C. The sheath 6 according to the present embodiment is referred to as a sheath 6C.

Figure 17:
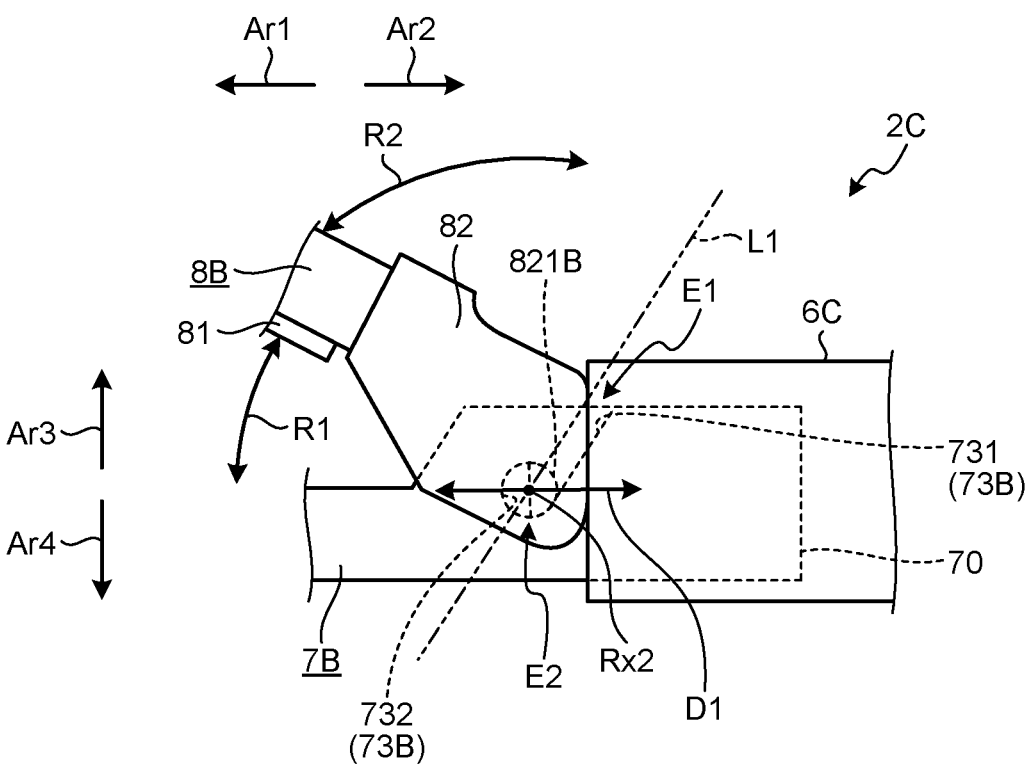
FIG. 17 is a view illustrating a function of a sheath according to an exemplary embodiment.

FIG. 17 is a diagram illustrating a function of the sheath 6C according to the present embodiment. Specifically, FIG. 17 is a view that corresponds to FIG. 16.

The method of assembling the treatment tool 2C according to the present embodiment is similar to the method of assembling the treatment tool 2B described in the above embodiment (FIGS. 14-16).

In the present embodiment, after completion of step S1D, the sheath 6C is disposed at the position illustrated in FIG. 17. In the state where the sheath 6C is located at the position illustrated in FIG. 17, the second gripping piece 8B pivots in the closing direction about the second pivot shaft Rx2 from the state illustrated in FIG. 15, and the chord of the semicircular shape in the pivot shaft 821B intersects the first straight line L1.

That is, the sheath 6C allows the pivot operation in a first range R1 in the closing direction of the second gripping piece 8B from the state illustrated in FIG. 17, and restricts the pivot operation in a second range R2 in the opening direction of the second gripping piece 8B from the state illustrated in FIG. 17.

In addition, the second gripping piece 8B is attachable to and detachable from the first gripping piece 7B at a pivoting position (position illustrated in FIG. 15) within the second range R2.

With the present embodiment, effects similar to the effects of the above-described embodiments can be achieved.

Next, another exemplary embodiment will be described.

In the following description, identical reference numerals are given to the components similar to those in the embodiments described above, and detailed description thereof will be omitted or simplified.

The present embodiment is different from the above-described embodiment shown in FIGS. 14-16 in the structure for attaching the second gripping piece 8B to the first gripping piece 7B.

Hereinafter, for convenience of description, the treatment tool 2 according to the present embodiment is referred to as a treatment tool 2D. In addition, the second gripping piece 8 according to the present embodiment will be referred to as a second gripping piece 8D.

Figure 18:
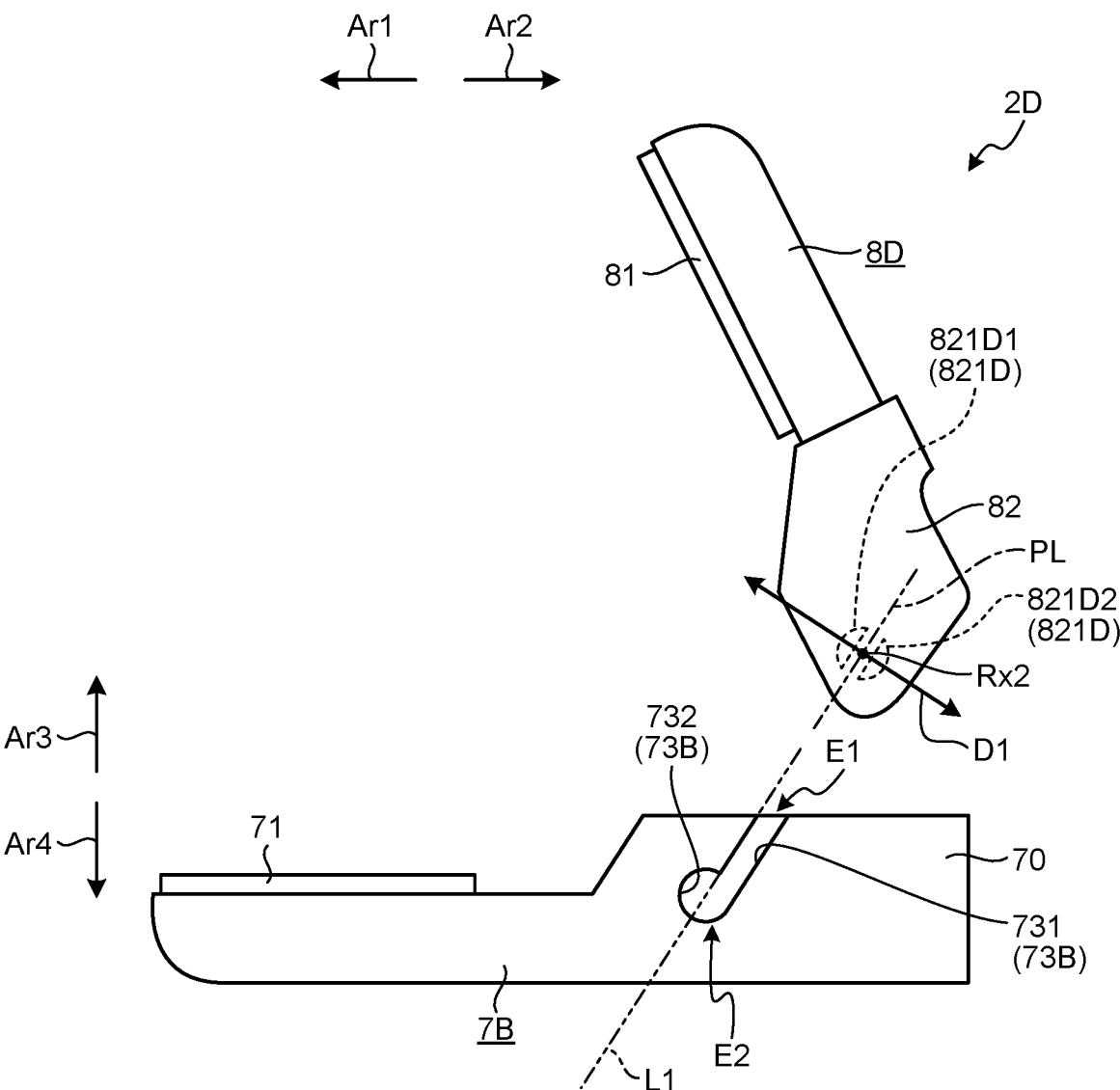
FIG. 18 is a view illustrating an attachment structure used to attach the second gripping piece to the first gripping piece according to an exemplary embodiment.
Figure 19:
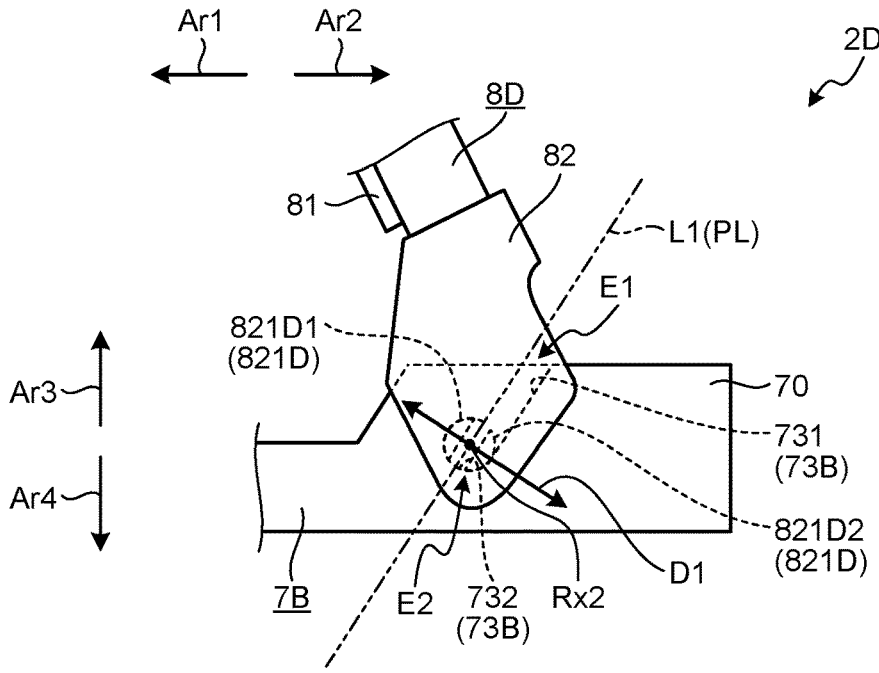
FIG. 19 is a view illustrating an attachment structure used to attach the second gripping piece to the first gripping piece according to an exemplary embodiment.
Figure 20:
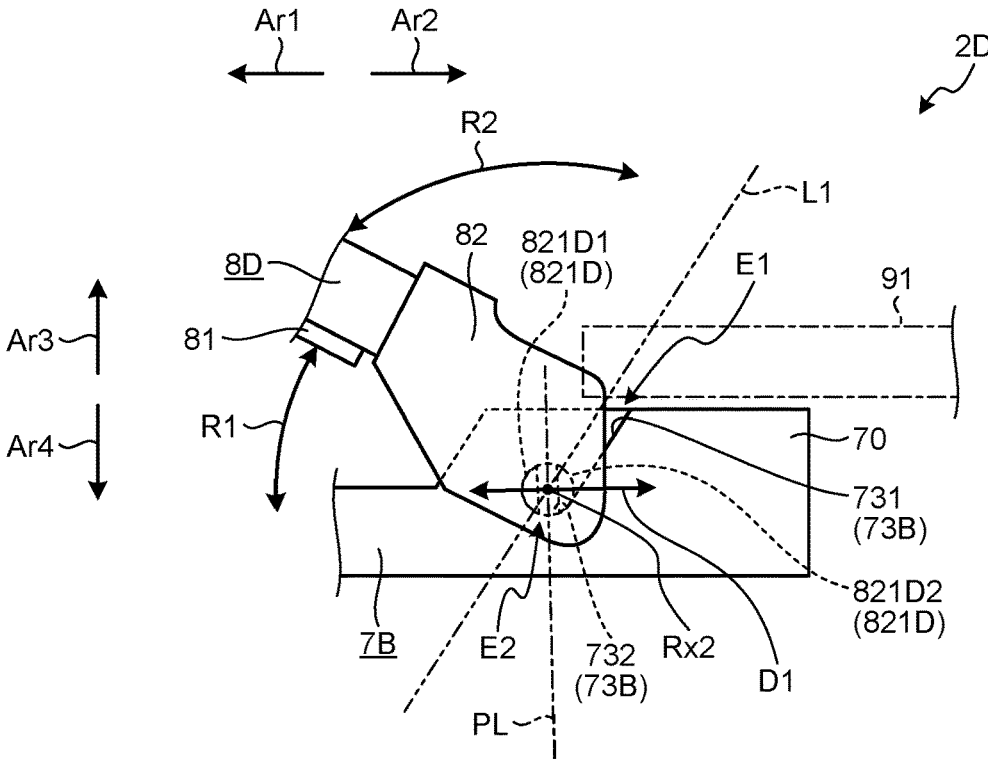
FIG. 20 is a view illustrating an attachment structure used to attach the second gripping piece to the first gripping piece according to an exemplary embodiment.

FIGS. 18 to 20 are views illustrating an attachment structure used to attach the second gripping piece 8D to the first gripping piece 7B. Specifically, FIGS. 18 to 20 are views of the first and second gripping pieces 7B and 8D viewed along the second pivot shaft Rx2.

In the second gripping piece 8D, the shape of the pivot shaft 821B is different from that of the second gripping piece

8B described in the above-described embodiment (FIGS. 14-16). Hereinafter, for convenience of description, the pivot shaft 821B according to the present embodiment will be referred to as a pivot shaft 821D.

The pivot shaft 821D is formed by dividing a cylinder protruding along the second pivot shaft Rx2 into two bodies at a boundary being a plane PL (FIGS. 18 to 20) that passes through a central axis (second pivot shaft Rx2) of the cylinder and is orthogonal to the first direction D1. Hereinafter, one of the two divided cylinders will be referred to as a first pivot shaft 821D1, and the other will be referred to as a second pivot shaft 821D2. The first and second pivot shafts 821D1 and 821D2 face each other in the first direction D1 and are elastically deformable in the first direction D1. In the present embodiment, the diameter of the bottom surface of the cylinder constituting the entire pivot shaft 821D is larger than the width dimension of the insertion portion 731. In addition, the outer dimension in the first direction D1 in a state where the first and second pivot shafts 821D1 and 821D2 are elastically deformed in a direction of approaching each other to the maximum is slightly smaller than the width dimension of the insertion portion 731.

In the method of assembling the treatment tool 2D according to the present embodiment, step S1A has a difference compared with step S1A in the method for assembling the treatment tool 2B described in the above embodiment (FIGS. 14-16).

In step S1A according to the present embodiment, the worker attaches the second gripping piece 8D to the first gripping piece 7B as described below.

That is, as illustrated in FIG. 18, when viewed in the direction along the second pivot shaft Rx2, the worker sets the second gripping piece 8D in a posture in which the first direction D1 is orthogonal to the first straight line L1, in other words, a posture in which the plane PL is parallel to the first straight line L1. Subsequently, as illustrated in FIGS. 18 and 19, the worker presses the pivot shaft 821D into the bearing 73B from the starting end E1 in the insertion portion 731 while maintaining the posture. With this operation, the first and second pivot shafts 821D1 and 821D2 are inserted into the insertion portion 731 while being elastically deformed in directions approaching each other by the inner wall surface of the insertion portion 731. After have moved to the bearing body 732, the first and second pivot shafts 821D1 and 821D2 no more interfere with the inner wall surface of the insertion portion 731 and thus return to the original shapes. The posture of the second gripping piece 8D illustrated in FIGS. 18 and 19 is a posture in which the distal end of the second gripping piece 8D is located on the upper side Ar3 with respect to the second pivot shaft Rx2, similarly to the posture of the second gripping piece 8 described in the above-described embodiment illustrated in FIGS. 4 and 5.

With the above step S1A, the second gripping piece 8D is attached to the first gripping piece 7B in a state where the pair of first connectors 70 is housed inside the U-shaped cross section formed by the pair of second connectors 82 and the base 83.

When step S1D is completed, the drive portion 91 is positioned at the position illustrated in FIG. 20. Specifically, the position illustrated in FIG. 20 is a limit position that allows the drive portion 91 to move toward the proximal end side Ar2 in a state where the operator has performed the opening operation on the movable handle 5. In the state where the drive portion 91 is located at the limit position, the second gripping piece 8D pivots in the closing direction about the second pivot shaft Rx2 from the state illustrated in FIG. 19, and the plane PL intersects the first straight line L1.

That is, the drive portion 91 allows the pivot operation in a first range R1 in the closing direction of the second gripping piece 8D from the state illustrated in FIG. 20, and restricts the pivot operation in a second range R2 in the opening direction of the second gripping piece 8D from the state illustrated in FIG. 20.

In addition, the second gripping piece 8D is attachable to and detachable from the first gripping piece 7B at a pivoting position (position illustrated in FIG. 19) within the second range R2.

Furthermore, when the second gripping piece 8D is located at the attachment-detachment position (the position illustrated in FIG. 19) which is the pivoting position where the second gripping piece 8D is attachable to and detachable from the first gripping piece 7B, the pivot shaft 821D is allowed to move from the bearing body 732 to the insertion portion 731 by elastic deformation of the first and second pivot shafts 821D1 and 821D2 in the direction of approaching each other. That is, the second gripping piece 8D is detachable from the first gripping piece 7B.

In contrast, when the second gripping piece 8D is located at the pivoting position within the first range R1, because of interference with the inner wall surface of the insertion portion 731, the pivot shaft 821D is not allowed to move from the bearing body 732 to the insertion portion 731. That is, the second gripping piece 8D is not detachable from the first gripping piece 7B.

Note that, the method of disassembling the treatment tool 2D performs reverse of individual steps of the above-described method of assembling the treatment tool 2D, and thus, description will be omitted.

With the present embodiment, effects similar to the effects of the above-described embodiments can be achieved.

Next, another exemplary embodiment will be described.

In the following description, identical reference numerals are given to the components similar to those in the embodiment described above (and shown in FIGS. 1-10), and detailed description thereof will be omitted or simplified.

The present embodiment is different from the above embodiment (FIGS. 1-10) in the structure for attaching the second gripping piece 8 to the first gripping piece 7.

Hereinafter, for convenience of description, the treatment tool 2 according to the present embodiment is referred to as a treatment tool 2E. In addition, the first gripping piece 7 according to the present embodiment will be referred to as a first gripping piece 7E. Furthermore, the second gripping piece 8 according to the present embodiment will be referred to as a second gripping piece 8E.

Figure 21:
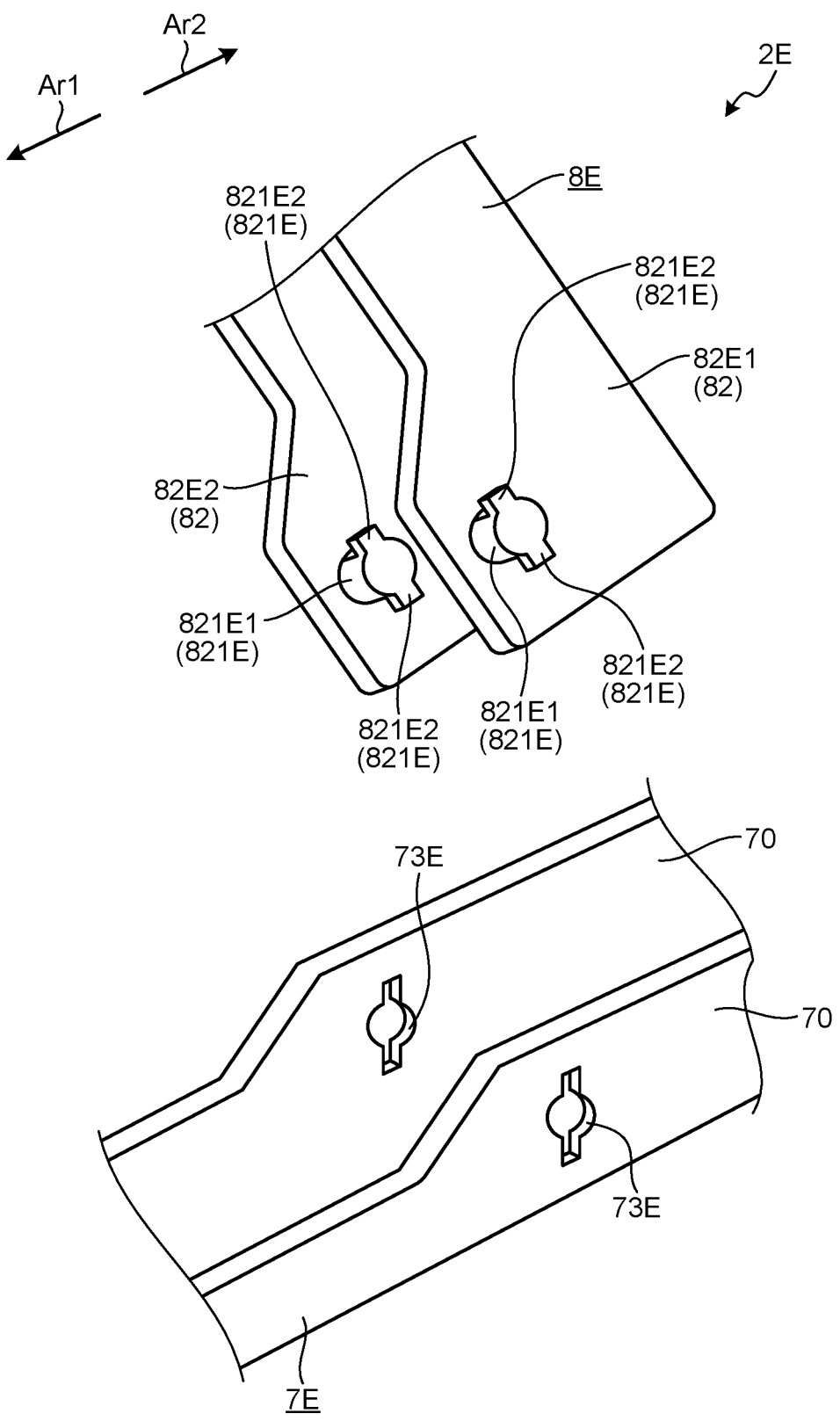
FIG. 21 is a view illustrating an attachment structure used to attach the second gripping piece to the first gripping piece according to an exemplary embodiment.
Figure 22:
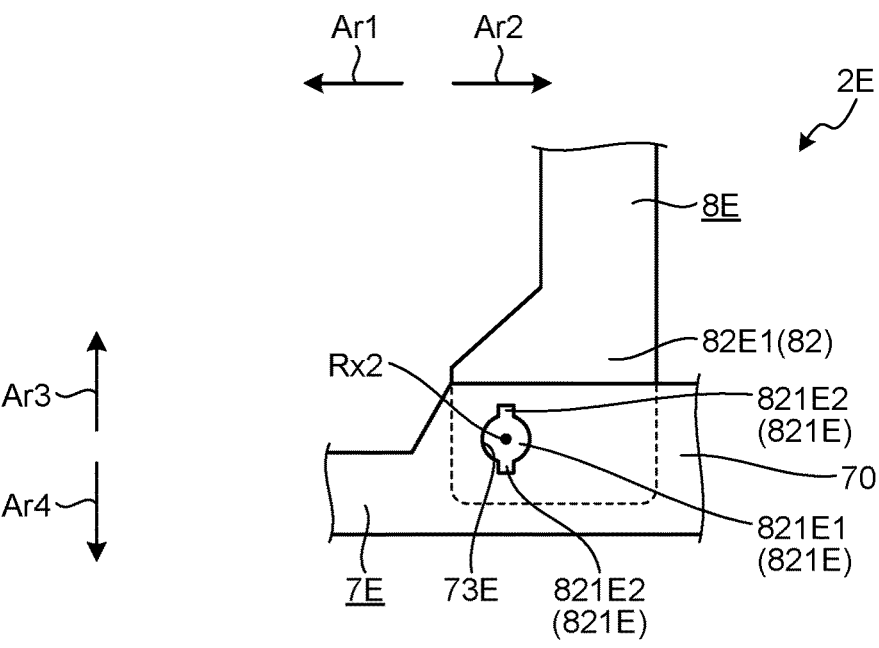
FIG. 22 is a view illustrating an attachment structure used to attach the second gripping piece to the first gripping piece according to an exemplary embodiment.
Figure 23:
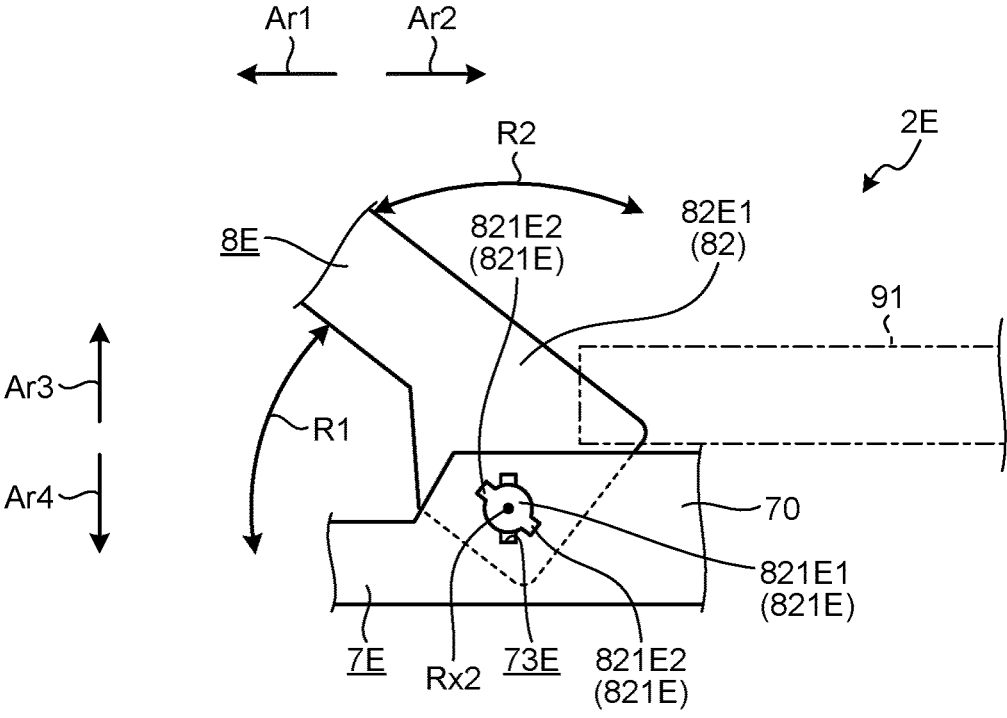
FIG. 23 is a view illustrating an attachment structure used to attach the second gripping piece to the first gripping piece according to an exemplary embodiment.

FIGS. 21 to 24 are views illustrating an attachment structure used to attach the second gripping piece 8E to the first gripping piece 7E. Specifically, FIG. 21 is an exploded perspective view illustrating the first and second gripping pieces 7E and BE. FIGS. 22 and 23 are views of the first and second gripping pieces 7E and 8E viewed along the second pivot shaft Rx2.

As compared with the first gripping piece 7 described in the above-described embodiment of FIGS. 1-10, the first gripping piece 7E has no arc portion 74 and has a bearing 73 having a shape different from the bearing 73 in the above embodiment. Hereinafter, for convenience of description, the bearing 73 according to the present embodiment will be referred to as a bearing 73E.

As compared with the second gripping piece 8 described in the above-described embodiment of FIGS. 1-10, the second gripping piece BE has no guide pin 822 and has a pivot shaft 821 having differences in shape and forming position from the pivot shaft 821 in the above embodiment.

Hereinafter, for convenience of description, the pivot shaft 821 according to the present embodiment will be referred to as a pivot shaft 821E.

A pair of pivot shafts 821E is provided on each of surfaces of a pair of second connectors 82 on the front side of the sheet surface of FIG. 21. The pair of second connectors 82 according to the present embodiment is shaped such that parallel displacement of one second connector 82 along the second pivot shaft Rx2 forms the other second connector 82. Hereinafter, for convenience of description, the second connector 82 on the front side on the sheet surface of FIG. 21 is referred to as a second connector 82E1, while the second connector 82 on the back side on the sheet surface of the drawing of FIG. 21 is referred to as a second connector 82E2.

As illustrated in FIG. 21, the pivot shaft 821E includes a pivot shaft body 821E1 and a pair of protrusions 821E2.

The pivot shaft body 821E1 has a cylindrical shape protruding along the second pivot shaft Rx2. The pivot shaft body 821E1 is a pivot center of the second gripping piece 8E.

The pair of protrusions 821E2 protrudes in directions away from each other from the end on the tip side of the outer surface of the pivot shaft body 821E1. When viewed in the direction along the second pivot shaft Rx2, the width dimension of the pair of protrusions 821E2 in a direction orthogonal to the protruding direction is smaller than the diameter of the pivot shaft body 821E1.

The bearing 73E, being a through hole that penetrates through the front-back of the first connector 70, has an inner shape following the outer shape of the pivot shaft 821E when viewed in the direction along the second pivot shaft Rx2, so as to be a through hole through which the pivot shaft 821E can be inserted.

In the method of assembling the treatment tool 2E according to the present embodiment, step S1A has a difference compared with step S1A in the method for assembling the treatment tool 2 described in the above embodiment (FIG. 8).

In step S1A according to the present embodiment, the worker attaches the second gripping piece 8E to the first gripping piece 7E as described below.

That is, as illustrated in FIG. 22, the worker inserts the second connector 82E1 between the pair of first connectors 70, and sets the second gripping piece 8E in a posture in which the pivot shaft 821E matches the bearing 73E when viewed in the direction along the second pivot shaft Rx2. Subsequently, the worker inserts the pivot shaft 821E into the bearing 73E while maintaining the posture. The posture of the second gripping piece 8E illustrated in FIG. 22 is a posture in which the distal end of the second gripping piece 8E is located on the upper side Ar3 with respect to the second pivot shaft Rx2, similarly to the posture of the second gripping piece 8 described in the above-described embodiment illustrated in FIGS. 4 and 5.

With the above step S1A, the second gripping piece BE is attached to the first gripping piece 7E in a state where only the second connector 82E1 is housed between the pair of first connectors 70.

When step S1D is completed, the drive portion 91 is positioned at the position illustrated in FIG. 23. Specifically, the position illustrated in FIG. 23 is a limit position that allows the drive portion 91 to move toward the proximal end side Ar2 in a state where the operator has performed the opening operation on the movable handle 5. In the state where the drive portion 91 is located at the limit position, the second gripping piece 8E pivots in the closing direction about the second pivot shaft Rx2 from the state illustrated in FIG. 22, forming a state where the bearing 73E and the pivot shaft 821E do not match each other when viewed in the direction along the second pivot shaft Rx2.

That is, the drive portion 91 allows the pivot operation in a first range R1 in the closing direction of the second gripping piece BE from the state illustrated in FIG. 23, and restricts the pivot operation in a second range R2 in the opening direction of the second gripping piece BE from the state illustrated in FIG. 23.

In addition, the second gripping piece BE is attachable to and detachable from the first gripping piece 7E at a pivoting position (position illustrated in FIG. 22) within the second range R2.

Furthermore, when the second gripping piece 8E is located at the attachment-detachment position (the position illustrated in FIG. 22), which is the pivoting position where the second gripping piece 8E can be attached to and detached from the first gripping piece 7E, the bearing 73E and the pivot shaft 821E match each other as viewed in the direction along the second pivot shaft Rx2. That is, the second gripping piece 8E is detachable from the first gripping piece 7E.

On the other hand, when the second gripping piece 8E is located at the pivoting position in the first range R1, the bearing 73E and the pivot shaft 821E do not match each other when viewed in the direction along the second pivot shaft Rx2. That is, because the protrusion 821E2 interferes with the first connector 70, the second gripping piece 8E is not detachable from the first gripping piece 7E.

Note that, the method of disassembling the treatment tool 2E performs reverse of individual steps of the above-described method of assembling the treatment tool 2E, and thus, description will be omitted.

With the present embodiment, effects similar to the effects of the above-described embodiment of FIGS. 1-10 can be achieved.

Next, another exemplary embodiment will be described.

In the following description, identical reference numerals are given to the components similar to those in the embodiment described above and shown in FIGS. 1-10, and detailed description thereof will be omitted or simplified.

In the present embodiment, treatment energy applied to a target site is different from that in the embodiment described above.

Hereinafter, for convenience of description, the treatment system 1 according to the present embodiment will be referred to as a treatment system 1F. In addition, the treatment tool 2 according to the present embodiment will be referred to as a treatment tool 2F.

Figure 24:
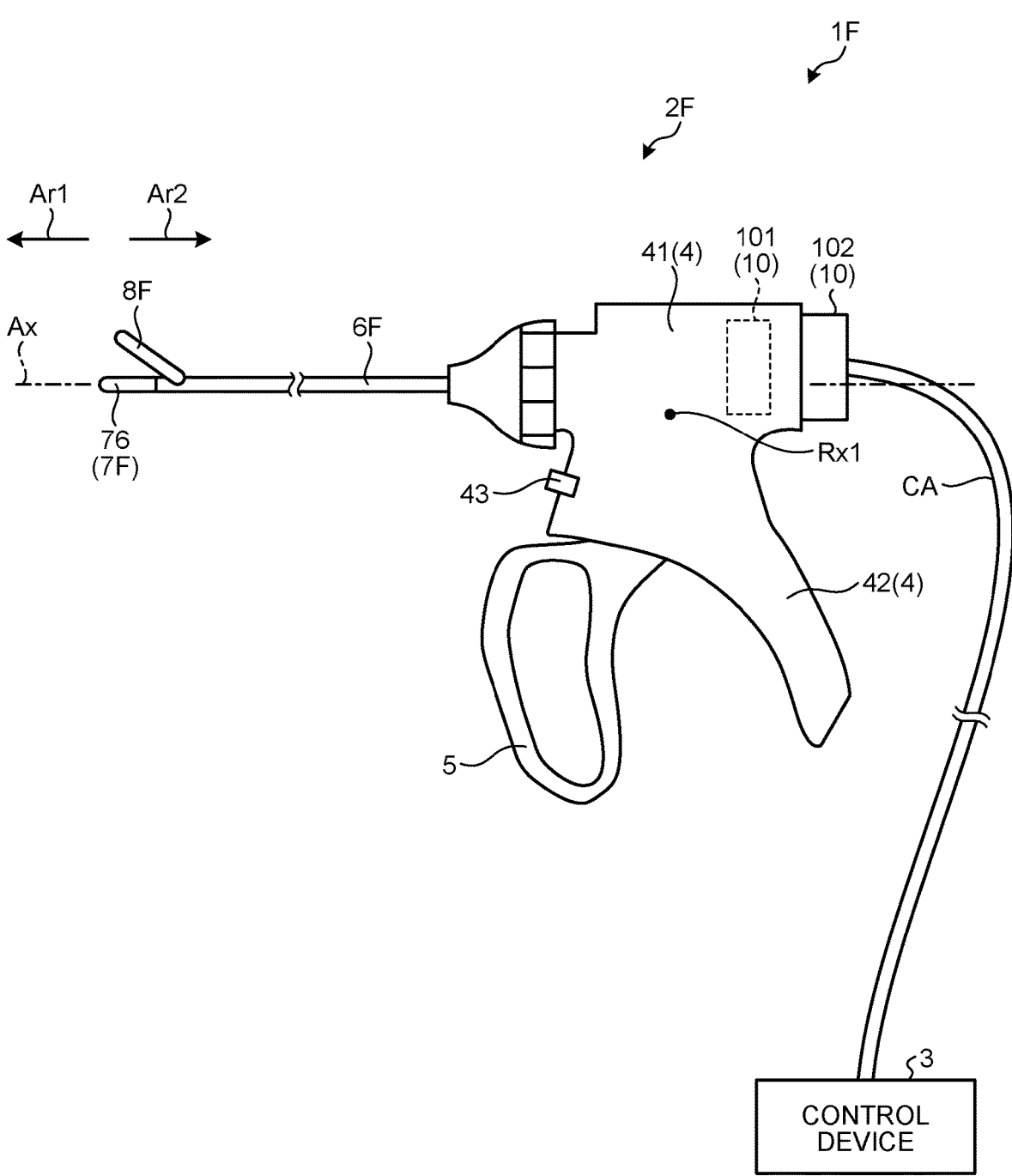
FIG. 24 is a view illustrating a treatment tool according to an exemplary embodiment.

FIG. 24 is a view illustrating the treatment system 1F according to the present embodiment.

In the treatment system 1F (treatment tool 2F), ultrasound energy is adopted as treatment energy. As compared with the treatment tool 2 described in the above-described embodiment of FIGS. 1-10, the treatment tool 2F (FIG. 24) adopts a vibration transmitting portion 7F, a movable gripping piece 8F, a drive portion 91F, and a sheath 6F instead of the first and second gripping pieces 7 and 8, the drive portion 91, and the sheath 6, respectively. Furthermore, the treatment tool 2F further includes an ultrasound transducer 10 (FIG. 24).

The vibration transmitting portion 7F has an elongated shape extending along the longitudinal axis Ax, and is inserted into the sheath 6F in a state where the end portion of the member on the distal end side Ar1 is exposed to the outside as illustrated in FIG. 24. The end portion on the distal end side Ar1 is a portion that grips the target site together with the movable gripping piece 8F, and corresponds to a fixed gripping piece 76 (FIG. 24). Furthermore, the end of the vibration transmitting portion 7F on the proximal end side Ar2 is connected to a bolt-tightened Langevin transducer (BLT) 101 included in the ultrasound transducer 10 (FIG. 24). Subsequently, the vibration transmitting portion 7F transmits the ultrasound vibration generated by the BLT 101 from the end of the proximal end side Ar2 to the fixed gripping piece 76. In the present embodiment, the ultrasound vibration is a longitudinal vibration that vibrates in the direction along the longitudinal axis Ax.

The ultrasound transducer 10 is inserted into the housing body 41 from the proximal end side Ar2 of the housing body 41 and is detachably connected to the housing body 41. The ultrasound transducer 10 includes: a transducer (TD) case 102 constituting an exterior of the ultrasound transducer 10; and a BLT 101 provided in the TD case 102 and configured to generate ultrasound vibration in accordance with AC power supply.

Here, the control device 3 is electrically connected to the BLT 101 via the electric cable CA. Subsequently, in response to the operation signal input from the switch 43, the control device 3 supplies AC power to the BLT 101 via the electric cable CA. With this operation, ultrasound vibration is applied from the fixed gripping piece 76 to the target site gripped between the fixed gripping piece 76 and the movable gripping piece 8F. In other words, ultrasound energy is applied from the fixed gripping piece 76 to the target site.

Figure 25:
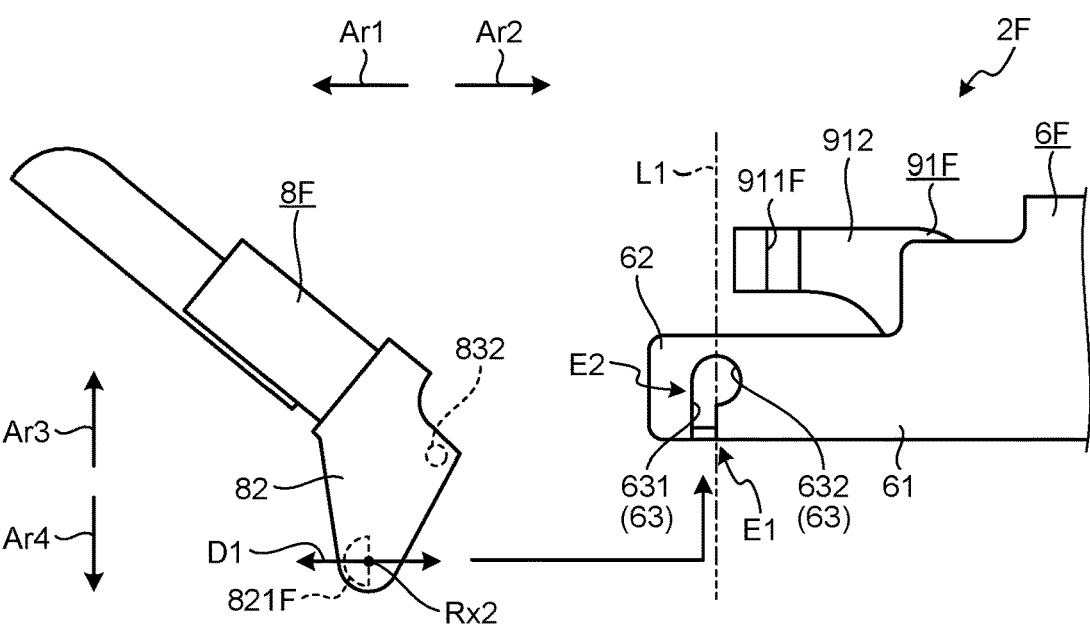
FIG. 25 is a view illustrating an attachment structure used to attach a movable gripping piece to a sheath.
Figure 26:
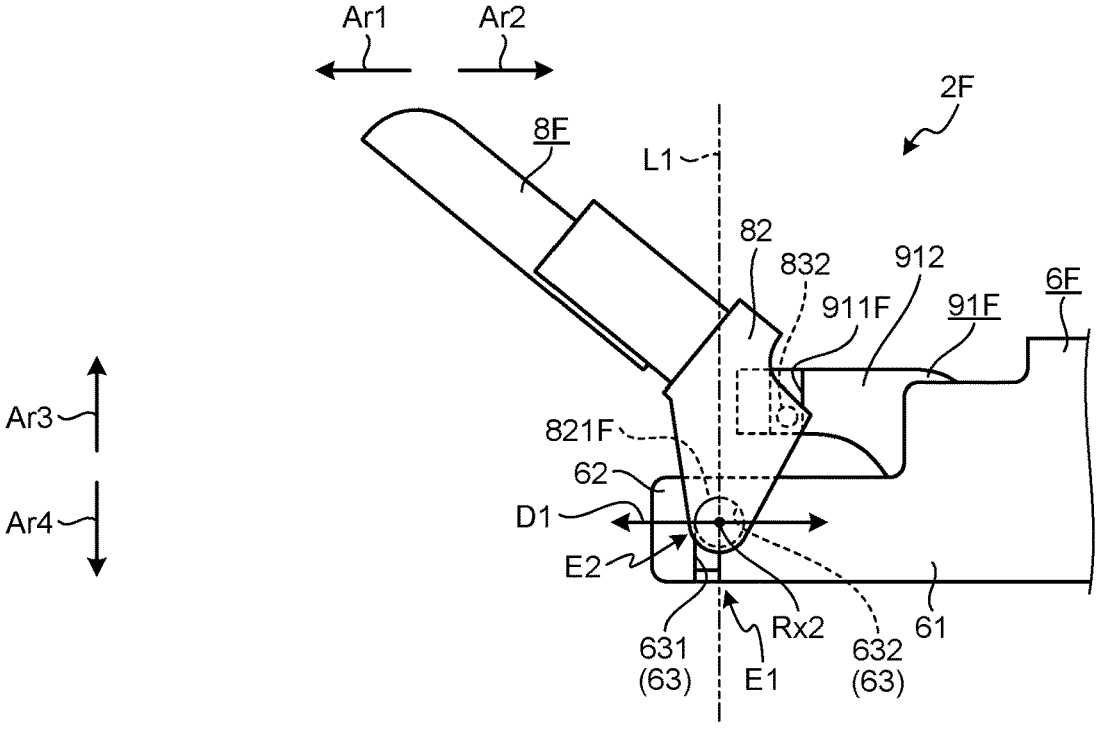
FIG. 26 is a view illustrating an attachment structure used to attach a movable gripping piece to a sheath.
Figure 27:
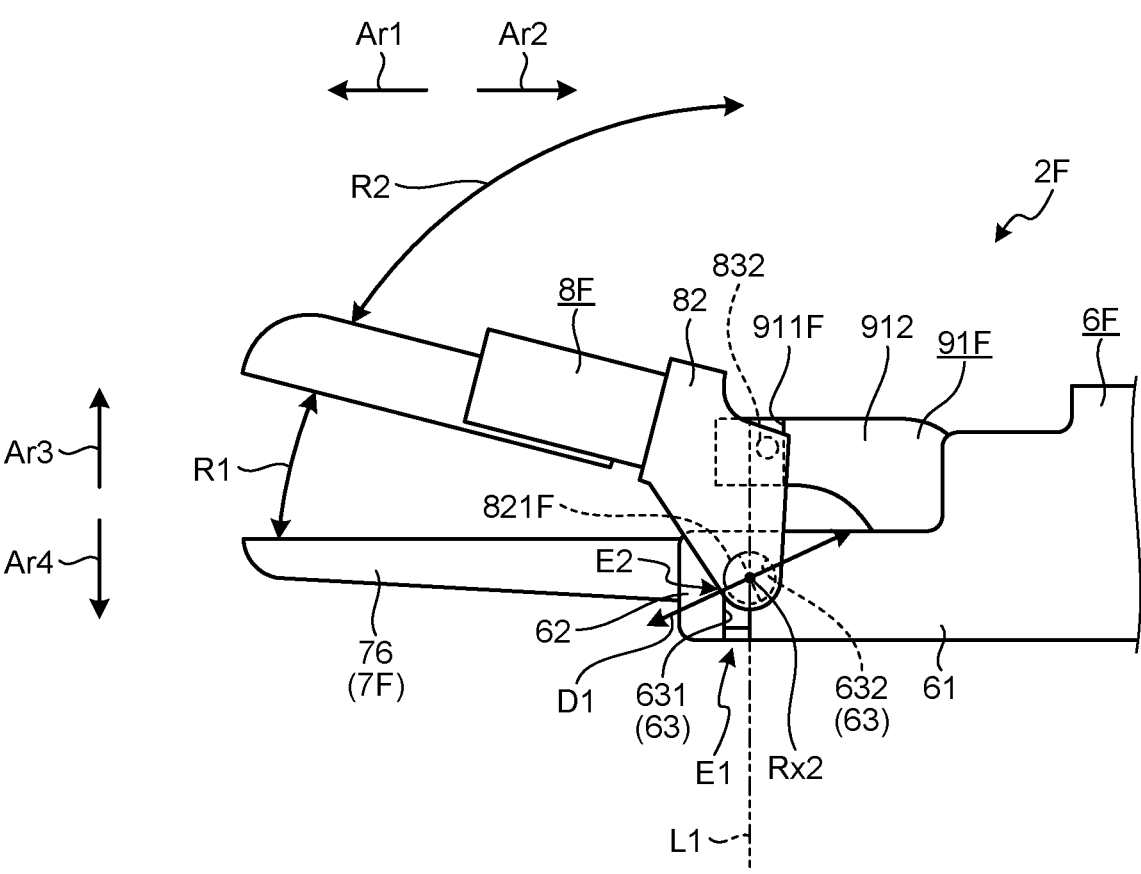
FIG. 27 is a view illustrating an attachment structure used to attach a movable gripping piece to a sheath.

FIGS. 25 to 27 are views illustrating an attachment structure used to attach the movable gripping piece 8F to the sheath 6F. Specifically, FIGS. 25 to 27 are views of the end of the treatment tool 2F on the distal end side Ar1 along the second pivot shaft Rx2.

In the present embodiment, the movable gripping piece 8F is attached to the sheath 6F as illustrated in FIGS. 24 to 27.

As compared with the second gripping piece 8 described in the above-described embodiment of FIGS. 1-10, the movable gripping piece 8F has no second electrode 81 or guide pin 822 and has a pivot shaft 821 having a shape different from the pivot shaft 821 in the above embodiment. Hereinafter, for convenience of description, the pivot shaft 821 according to the present embodiment will be referred to as a pivot shaft 821F.

Similarly to the pivot shaft 821B described in the embodiment shown in FIGS. 14-16, the pivot shaft 821F protrudes along the second pivot shaft Rx2, and has a semicircular cross section taken along a plane orthogonal to the second pivot shaft Rx2.

Here, the direction orthogonal to the semicircular chord in the pivot shaft 821F corresponds to a first direction D1. That is, in the present embodiment, regarding the outer dimension of the pivot shaft 821F in a direction orthogonal to the second pivot shaft Rx2, the outer dimension in the first direction D1 (the radius of the semicircular shape in the pivot shaft 821F) is the smallest.

At an end of the sheath 6F on the distal end side Ar1, there is provided an extending portion 61 in which only a part of the lower side Ar4 of the sheath 6F is extended toward the distal end side Ar1.

As illustrated in FIGS. 25 to 27, the extending portion 61 has a pair of side walls 62 intersecting the second pivot shaft Rx2, and there is provided a bearing 63 on each of the side walls 62. The pair of side walls 62 has a shape symmetrical to each other with respect to a plane parallel to the sheet surfaces of FIGS. 25 to 27.

As illustrated in FIGS. 25 to 27, the bearing 63 includes an insertion portion 631 and a bearing body 632.

The insertion portion 631 extends along a first straight line L1 (FIGS. 25 to 27) intersecting the second pivot shaft Rx2 from the outer edge (hereinafter, referred to as a starting end E1 (FIGS. 25 to 27)) of the side wall 62 on the lower side Ar4. The insertion portion 631 allows the pivot shaft 821F to be inserted along the first straight line L1 from the starting end E1. In the present embodiment, the width dimension of the insertion portion 631 is slightly larger than the radius of the semicircular shape of the pivot shaft 821F and smaller than the diameter of the semicircular shape. The first straight line L1 is a straight line toward the upper side Ar3 when viewed in the direction along the second pivot shaft Rx2. Furthermore, the insertion portion 631 is formed by a through hole penetrating the side wall 62.

Similarly to the insertion portion 631, the bearing body 632 is formed of a through hole, and communicates with the terminating end E2 of insertion portion 631 on the upper side Ar3. The bearing body 632 has a circular shape with a width dimension of the insertion portion 631 as a radius when viewed in a direction along the second pivot shaft Rx2. The bearing body 632 pivotally and pivotably supports the pivot shaft 821F (movable gripping piece 8F).

Figure 28:
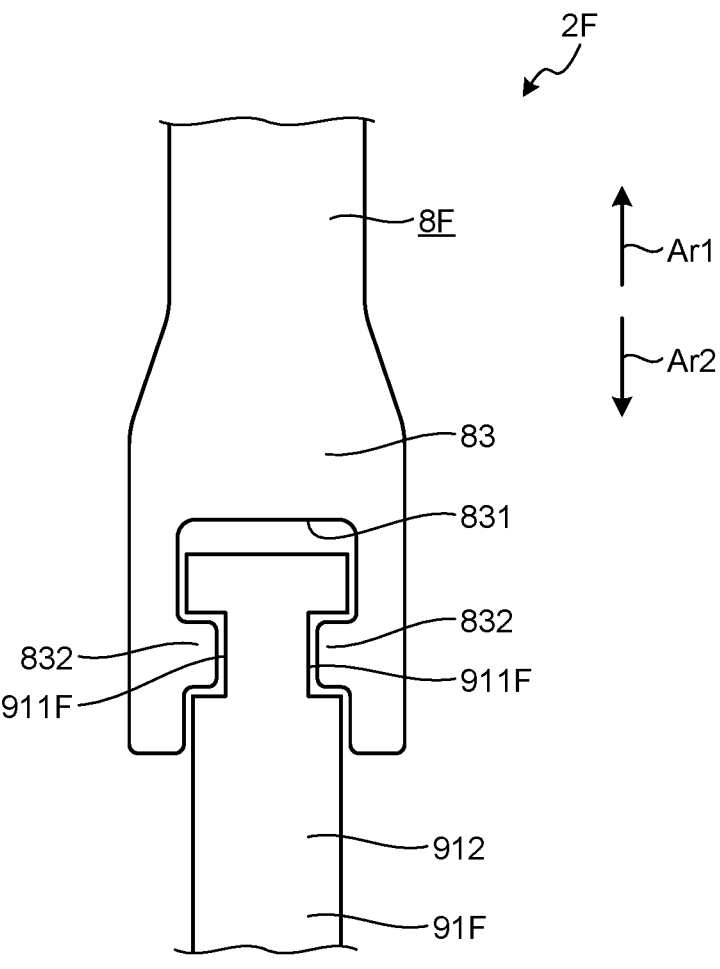
FIG. 28 is a view illustrating an engagement structure between a movable gripping piece and a drive portion.

FIG. 28 is a view illustrating an engagement structure between the movable gripping piece 8F and the drive portion 91F. Specifically, FIG. 28 is a view illustrating the engagement structure between the movable gripping piece 8F and the drive portion 91F as seen from the upper side Ar3.

The drive portion 91F has a cylindrical shape extending along the longitudinal axis Ax. The vibration transmitting portion 7F is inserted into the drive portion 91F.

As illustrated in FIGS. 25 to 28, at an end of the drive portion 91F on the distal end side Ar1, there is provided an arm 912 protruding from the upper side Ar3 toward the distal end side Ar1.

The arm 912 is provided with engagement grooves 911F (FIGS. 25 to 28) respectively extending in directions (directions orthogonal to the sheet surface of FIG. 28) orthogonal to each of the protruding direction of the engagement pin 832 and the longitudinal axis Ax, each of the engagement grooves 911F configured to be engaged with each of the engagement pins 832.

When the drive portion 91F moves along the longitudinal axis Ax in a state where the engagement pin 832 and the engagement groove 911F are engaged with each other, the movable gripping piece 8F performs open-close operation with respect to the fixed gripping piece 76 about the second pivot shaft Rx2.

Next, a method of assembling the treatment tool 2F will be described.

FIG. 29 is a flowchart illustrating a method of assembling the treatment tool 2F.

First, the worker inserts the drive portion 91F from the proximal end side Ar2 of the sheath 6F into the sheath 6F (step S4A).

Next, as described below, the worker attaches the movable gripping piece 8F to the sheath 6F (step S4B).

That is, as illustrated in FIG. 25, when viewed in the direction along the second pivot shaft Rx2, the worker sets the movable gripping piece 8F in a posture in which the first direction D1 is orthogonal to the first straight line L1, in other words, a posture in which the chord of the semicircular shape in the pivot shaft 821F is parallel to the first straight line L1. Subsequently, as illustrated in FIGS. 25 and 26, the worker inserts the pivot shaft 821F into the bearing 63 from the starting end E1 of the insertion portion 631 while maintaining the posture. The posture of the movable gripping piece 8F illustrated in FIGS. 25 and 26 is a posture in which the distal end of the movable gripping piece 8F is located on the upper side Ar3 with respect to the second pivot shaft Rx2, similarly to the posture of the second gripping piece 8 described in the above-described embodiment illustrated in FIGS. 4 and 5.

With the above step S4B, the movable gripping piece 8F is attached to the sheath 6F in a state where the extending portion 61 is housed inside the U-shaped cross section formed by the pair of second connectors 82 and the base 83.

Together with step S4B, the worker engages the movable gripping piece 8F with the drive portion 91F as described below (step S4C).

That is, the worker inserts the pivot shaft 821F into the bearing 63 (step S4B) and together with this, inserts the pair of engagement pins 832 into the pair of engagement grooves 911F. This allows the movable gripping piece 8F to be engaged with the drive portion 91F as illustrated in FIG. 28.

After step S4C, the worker inserts the vibration transmitting portion 7F into the drive portion 91F as illustrated in FIG. 27 (step S4D). With this operation, the vibration transmitting portion 7F has a state where the fixed gripping piece 76 protrudes from the distal end of the sheath 6F.

After step S4D, the worker assembles the ends of the drive portion 91F and the sheath 6F on the proximal end side Ar2 into the housing 4 (step S4E). This allows the drive portion 91F to be disposed at the position illustrated in FIG. 27. Specifically, the position illustrated in FIG. 27 is a limit position that allows the drive portion 91F to move toward the proximal end side Ar2 in a state where the operator has performed the opening operation on the movable handle 5. In the state where the drive portion 91F is located at the limit position, the movable gripping piece 8F pivots in the closing direction about the second pivot shaft Rx2 from the state illustrated in FIG. 26, and the chord of the semicircular shape in the pivot shaft 821F intersects the first straight line L1.

That is, the drive portion 91F allows the pivot operation in the first range R1 in the closing direction of the movable gripping piece 8F from the state illustrated in FIG. 27, and restricts the pivot operation in a second range R2 in the opening direction of the movable gripping piece 8F from the state illustrated in FIG. 27. Therefore, the drive portion 91F corresponds to the movement restricting portion.

In addition, the movable gripping piece 8F is attachable to and detachable from the fixed gripping piece 76 at a pivoting position (a position illustrated in FIG. 26) within the second range R2.

Furthermore, when the movable gripping piece 8F is located at an attachment-detachment position (a position illustrated in FIG. 26) which is a pivoting position where the movable gripping piece 8F can be attached to and detached from the fixed gripping piece 76, the pivot shaft 821F is movable from the bearing body 632 to the insertion portion 631. That is, the movable gripping piece 8F is detachable from the sheath 6F.

In contrast, when the movable gripping piece 8F is located at the pivoting position within the first range R1, because of interference with the inner wall surface of the insertion portion 631, the pivot shaft 821F is not allowed to move from the bearing body 632 to the insertion portion 631. That is, the movable gripping piece 8F is not detachable from the sheath 6F.

Next, a method of disassembling the treatment tool 2F will be described.

FIG. 30 is a flowchart illustrating a method of disassembling the treatment tool 2F.

Note that, the method of disassembling the treatment tool 2F performs reverse of individual steps of the above-described method of assembling the treatment tool 2F. Therefore, the method of disassembling the treatment tool 2F will be briefly described below.

First, the worker detaches the end of the drive portion 91F and the sheath 6F on the proximal end side Ar2 from inside the housing 4 (step S5A).

After step S5A, the worker extracts the vibration transmitting portion 7F from the inside of the drive portion 91 (step S5B).

After step S5B, the worker positions the movable gripping piece 8F at the attachment-detachment position (the position illustrated in FIG. 26), and moves the movable gripping piece 8F to the lower side Ar4 while maintaining the posture of the movable gripping piece 8F. Subsequently, the worker moves the engagement pin 832 to the lower side Ar4 in the engagement groove 911F to release the engagement between the engagement pin 832 and the engagement groove 911F (step S5C).

Together with step S5C, the worker moves the pivot shaft 821F toward the starting end E1 in the bearing 63, thereby detaching the movable gripping piece 8F from the sheath 6F (step S5D).

With the above-described present embodiment of the disclosure, effects similar to the effects of the above-described embodiment shown in FIGS. 1-10 can be achieved.

Next, another exemplary embodiment will be described.

In the following description, identical reference numerals are given to the components similar to those in the embodiments described above, and detailed description thereof will be omitted or simplified.

The present embodiment is different from the above-described embodiment shown in FIGS. 24-30 in the structure for attaching the movable gripping piece 8F to the sheath 6F.

Hereinafter, for convenience of description, the treatment tool 2F according to the present embodiment is referred to as a treatment tool 2G. In addition, the movable gripping piece 8F according to the present embodiment will be referred to as a movable gripping piece 8G.

Figure 31:
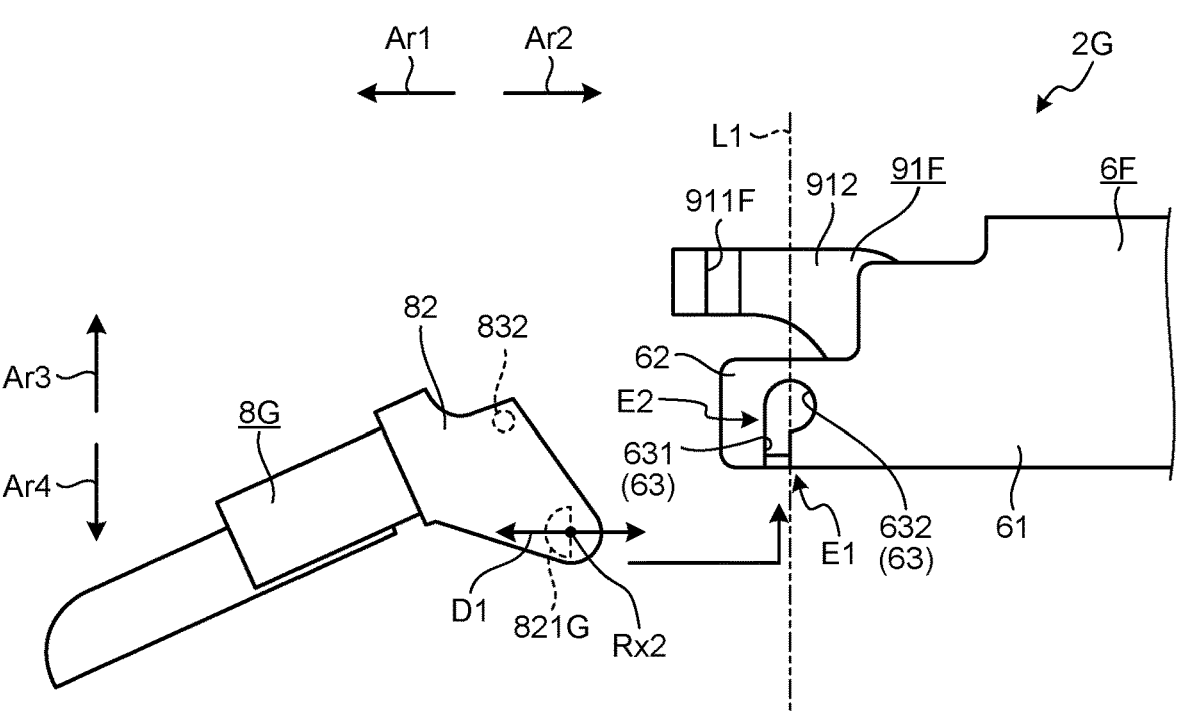
FIG. 31 is a view illustrating an attachment structure used to attach a movable gripping piece to a sheath according to an exemplary embodiment.
Figure 32:
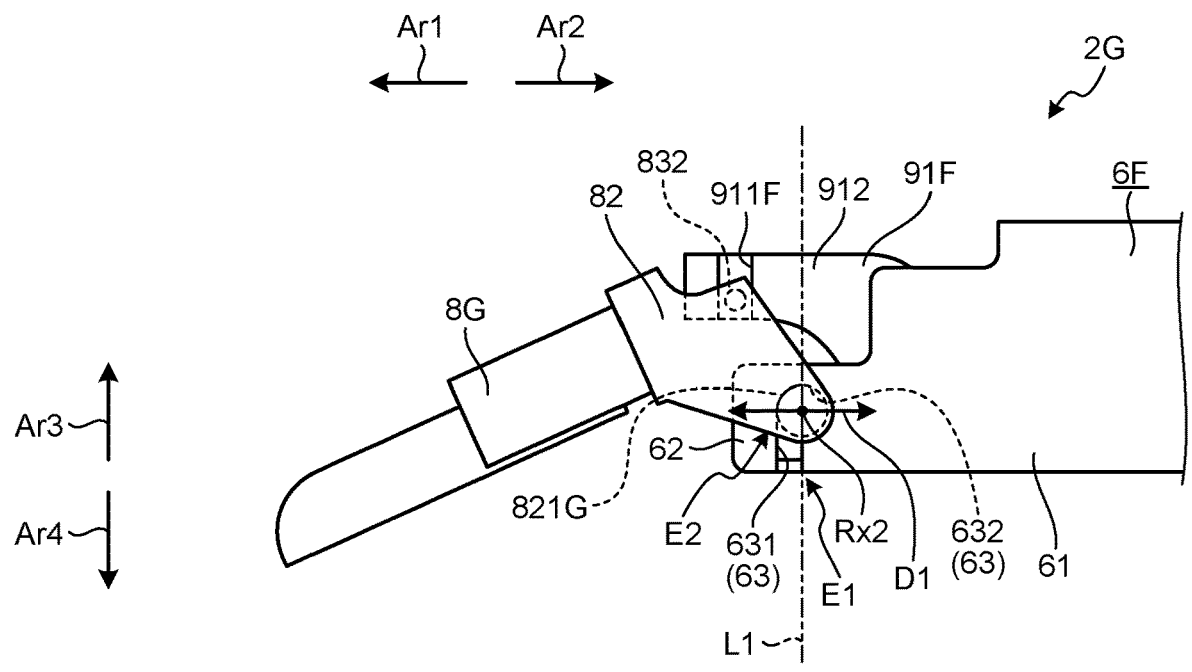
FIG. 32 is a view illustrating an attachment structure used to attach a movable gripping piece to a sheath according to an exemplary embodiment.
Figure 33:
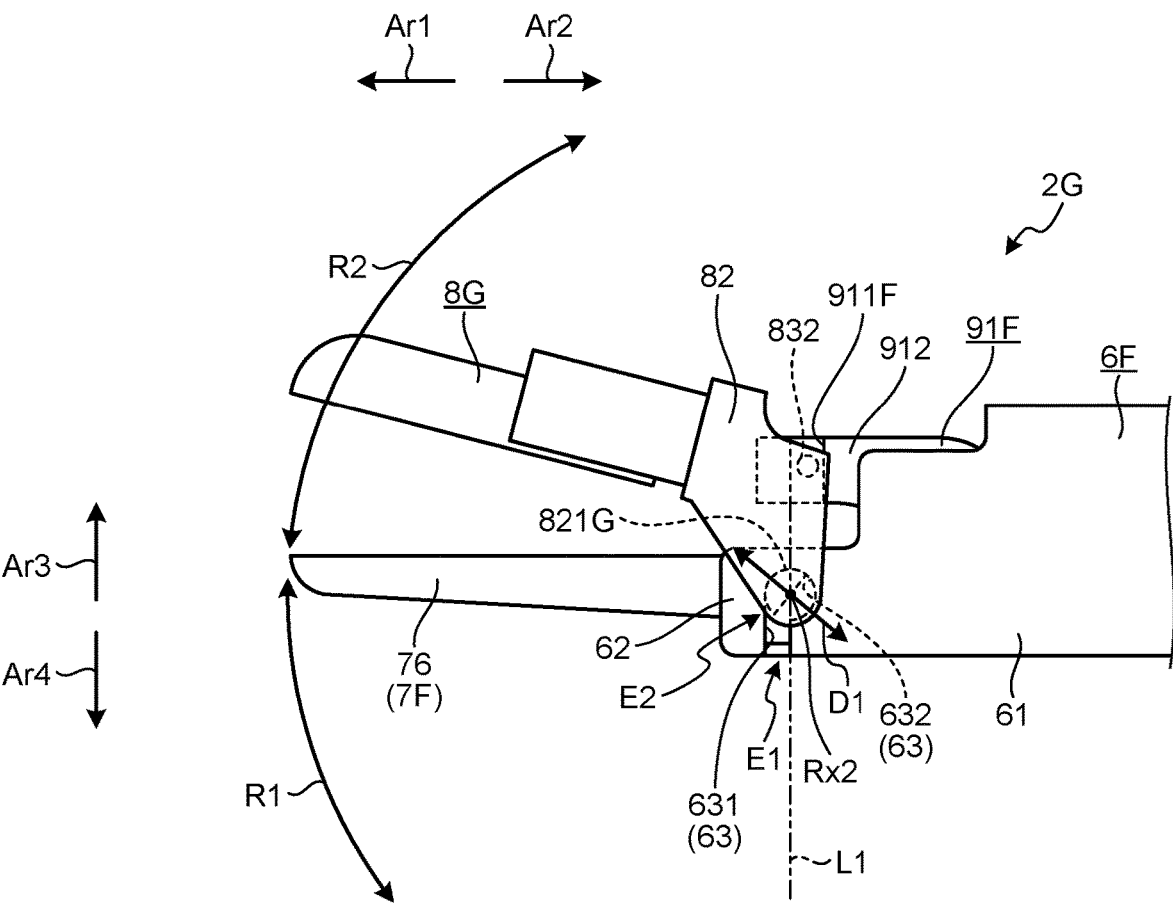
FIG. 33 is a view illustrating an attachment structure used to attach a movable gripping piece to a sheath according to an exemplary embodiment.

FIGS. 31 to 33 are views illustrating an attachment structure used to attach the movable gripping piece 8G to the sheath 6F. Specifically, FIGS. 31 to 33 are views of the end of the treatment tool 2G on the distal end side Ar1 along the second pivot shaft Rx2.

The movable gripping piece 8G is different from the movable gripping piece 8F in the above-described embodiment of FIGS. 24-30 only in that the pivot shaft 821F is rotated about the second pivot shaft Rx2 by approximately 90°. Hereinafter, for convenience of description, the pivot shaft 821F according to the present embodiment will be referred to as a pivot shaft 821G.

In the method of assembling the treatment tool 2G according to the present embodiment, step S4B has a difference compared with step S4B in the method for assembling the treatment tool 2F described above (FIG. 29).

That is, as illustrated in FIG. 31, when viewed in the direction along the second pivot shaft Rx2, the worker sets the movable gripping piece 8G in a posture in which the first direction D1 is orthogonal to the first straight line L1, in other words, a posture in which the chord of the semicircular shape in the pivot shaft 821G is parallel to the first straight line L1. Subsequently, as illustrated in FIGS. 31 and 32, the worker inserts the pivot shaft 821G into the bearing 63 from the starting end E1 of the insertion portion 631 while maintaining the posture. The posture of the movable gripping piece 8G illustrated in FIGS. 31 and 32 is a posture in which the distal end of the movable gripping piece 8G is located on the lower side Ar4 with respect to the second pivot shaft Rx2.

With the above step S4B, the movable gripping piece 8G is attached to the sheath 6F in a state where the extending portion 61 is housed inside the U-shaped cross section formed by the pair of second connectors 82 and the base 83 (FIG. 28).

In the present embodiment, after completion of step S4D, the movable gripping piece 8G pivots in the opening direction about the second pivot shaft Rx2 from the state illustrated in FIG. 32, and the semicircular chord of the pivot shaft 821G intersects the first straight line L1.

That is, the vibration transmitting portion 7F allows the pivot operation of the movable gripping piece 8G in the first range R1 in the opening direction of the movable gripping piece 8G from the state of being in contact with the fixed gripping piece 76, and restricts the pivot operation of the movable gripping piece 8G in the second range R2 in the closing direction of the movable gripping piece 8G from the state of being in contact.

In addition, the movable gripping piece 8G is attachable to and detachable from the sheath 6F at a pivoting position (position illustrated in FIG. 32) within the second range R2.

With the present embodiment, effects similar to the effects of the above-described embodiments can be achieved.

OTHER EXEMPLARY EMBODIMENTS

Embodiments of the disclosure have been described hereinabove. However, the disclosure is not intended to be limited to the above-described embodiments.

In the above-described embodiments, the treatment energy obtained by combining the thermal energy and the high-frequency energy or the treatment energy of only the ultrasound energy is exemplified as the treatment energy applied to the target site, but the treatment energy is not limited thereto. As the treatment energy, other treatment energies may be adopted as long as the treatment energy is at least one of thermal energy, high-frequency energy, and ultrasound energy.

In the above-described embodiments, the movable gripping piece (second gripping pieces 8, 8A, 8B, 8D, 8E, movable gripping pieces 8F, 8G) is pivotably attached to the sheath (sheath 6, 6C, 6F) or the fixed gripping piece (first gripping piece 7, 7A, 7B, 7E, and fixed gripping piece 76). However, the configuration is not limited thereto, and it is allowable to adopt a configuration in which the movable gripping piece is attached by a moving method other than pivoting.

According to the treatment tool, the treatment tool assembling method, and the treatment tool disassembling method of the disclosure, it is possible to facilitate assembly and disassembly.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment tool comprising:
a sheath extending along a longitudinal axis;
a fixed gripping piece located distally relative to a distal end of the sheath;
a movable gripping piece movably attached to either the sheath or the fixed gripping piece, the movable gripping piece including a first pin and a second pin; and
a movement restricting portion that includes a drive portion configured to allow movement of the movable gripping piece in a first range and restrict movement of the movable gripping piece in a second range different from the first range,
wherein:
the movable gripping piece is attachable to and detachable from either the sheath or the fixed gripping piece at a movement position within the second range, and
the first pin and the second pin are located in a slot provided on one of the sheath and the fixed gripped piece.

2. The treatment tool according to claim 1, wherein:
one of the sheath or the fixed gripping piece is a first member, and the movable gripping piece is a second member,
one of the first member and the second member includes a pivot shaft extending along a central axis so as to be a pivot center of the movable gripping piece,
another of the first member and the second member includes a bearing configured to pivotally support the pivot shaft, and
the movement restricting portion is configured to allow a pivot operation of the movable gripping piece in the first range and restrict a pivot operation of the movable gripping piece in the second range.

3. The treatment tool according to claim 2, wherein:
the bearing extends from an outer edge of the another of the first member and the second member along a first straight line intersecting the central axis when the movable gripping piece is attached, and is configured to allow the pivot shaft to be inserted from the outer edge along the first straight line,
the one of the first member and the second member further includes a guide pin configured to be insertable, together with the pivot shaft, into the bearing,
the other of the first member and the second member further includes an arc portion communicating with the bearing through which the guide pin can be inserted in accordance with the pivot operation of the movable gripping piece, the arc portion communicating with the bearing and extending in an arc shape about the pivot center,
when the movable gripping piece is located at a pivoting position which is an attachment-detachment position at which the movable gripping piece is attachable to and detachable from either the sheath or the fixed gripping piece, the guide pin is positioned in the bearing and is configured to allow a movement of the pivot shaft toward the outer edge, and
when the movable gripping piece is located at a pivoting position within the first range, the guide pin is positioned in the arc portion and is configured to restrict the movement of the pivot shaft toward the outer edge.

4. The treatment tool according to claim 2,
wherein the bearing is a groove extending from an outer edge of the other member along a first straight line intersecting the central axis.

5. The treatment tool according to claim 2, wherein:
the drive portion configured to be inserted into the sheath and configured to be movable along the longitudinal axis when inserted into the sheath,
the drive portion is configured to engage with the movable gripping piece and move along the longitudinal axis to allow a pivot operation of the movable gripping piece,
either one of the movable gripping piece or the drive portion includes an engagement pin protruding along the central axis, and
another of the movable gripping piece and the drive portion includes an engagement groove that extends in a direction orthogonal to both of a protruding direction of the engagement pin and a direction intersecting the longitudinal axis, the engagement groove being configured to be engaged with the engagement pin.

6. The treatment tool according to claim 2, wherein the slot includes a first slot and a second slot, the first slot communicates with the second slot.

7. The treatment tool according to claim 6, wherein the second slot extends intersecting with the first slot.

8. The treatment tool according to claim 6, wherein the second slot is arc shape.

9. The treatment tool according to claim 6, wherein, when the movable gripping piece is at a movement position within the first range, the first pin is located in the first slot and the second pin is located in the second slot.

10. The treatment tool according to claim 6, wherein, when the movable gripping piece is at the movement position within the second range, the first pin and the second pin are located in the first slot.

11. The treatment tool according to claim 2, wherein the second pin is configured to move in a longitudinal direction relative to the first pin.

12. The treatment tool according to claim 1, wherein the movement restricting portion is a elongate member, the elongate member is configured to advance towards the distal end of the sheath when restricting movement of the movable gripping piece in the second range.

13. A treatment tool comprising:
a sheath;
a fixed gripping piece located distally relative to a distal end of the sheath and including a first slot and a second slot communicating with a first groove; and
a movable gripping piece movably attached to the fixed gripping piece and a first pin and a second pin,
wherein, when the first pin and the second pin are located in the first slot, the movable gripping piece is configured to detach from the fixed gripping piece.

14. The treatment tool according to claim 13, wherein, when the first pin is located in the first slot and the second pin is located in the second slot, the movable gripping piece is movably attached to the fixed gripping piece.

15. The treatment tool according to claim 13, wherein the second slot extends intersecting with the first slot.

16. The treatment tool according to claim 15, wherein the first slot extends intersecting with a longitudinal axis.

17. The treatment tool according to claim 15, wherein the second pin is configured to move in a longitudinal direction relative to the first pin.

18. The treatment tool according to claim 15, wherein the second slot is arc shape.

19. The treatment tool according to claim 13, wherein the first slot extends intersecting with a longitudinal axis.

* * * * *